US009592492B2

(12) United States Patent
Biberger et al.

(10) Patent No.: US 9,592,492 B2
(45) Date of Patent: *Mar. 14, 2017

(54) METHOD AND SYSTEM FOR FORMING PLUG AND PLAY OXIDE CATALYSTS

(71) Applicant: SDCmaterials, Inc., Tempe, AZ (US)

(72) Inventors: Maximilian A. Biberger, Scottsdale, AZ (US); Stephen Edward Lehman, Jr., Spartanburg, SC (US); Robert Matthew Kevwitch, Tempe, AZ (US); Qinghua Yin, Tempe, AZ (US)

(73) Assignee: SDCmaterials, Inc., Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/745,272

(22) Filed: Jun. 19, 2015

(65) Prior Publication Data
US 2016/0144346 A1  May 26, 2016

Related U.S. Application Data

(63) Continuation of application No. 13/921,066, filed on Jun. 18, 2013, now Pat. No. 9,089,840, which is a (Continued)

(51) Int. Cl.
*B01J 23/46* (2006.01)
*B01J 37/08* (2006.01)
(Continued)

(52) U.S. Cl.
CPC .............. *B01J 23/464* (2013.01); *B01J 8/00* (2013.01); *B01J 21/04* (2013.01); *B01J 21/063* (2013.01);
(Continued)

(58) Field of Classification Search
None
See application file for complete search history.

(56) References Cited

U.S. PATENT DOCUMENTS

| 1,477,664 A | 12/1923 | Rankin |
| 2,021,936 A | 11/1935 | Johnstone |

(Continued)

FOREIGN PATENT DOCUMENTS

| CN | 1647858 A | 8/2005 |
| CN | 101011664 A | 8/2007 |

(Continued)

OTHER PUBLICATIONS

Ahmad, K. et al. (2008). "Hybrid Nanocomposites: A New Route Towards Tougher Alumina Ceramics," *Composites Science and Technology* 68: 1321-1327.
(Continued)

*Primary Examiner* — Sarah A Slifka
(74) *Attorney, Agent, or Firm* — Morrison & Foerster LLP

(57) ABSTRACT

An oxide catalyst is formed by vaporizing a quantity of at least one precursor material or catalyst material thereby forming a vapor cloud. The vapor cloud is quenched forming precipitate nanoparticles. The nanoparticles are impregnated onto supports. The supports are able to be used in existing heterogeneous catalysis systems. A system for forming oxide catalysts comprises means for vaporizing a quantity of at least one precursor material or at least one catalyst material, quenching the resulting vapor cloud and forming precipitate nanoparticles. The system further comprises means for supports with the nanoparticles.

14 Claims, 7 Drawing Sheets

Related U.S. Application Data continuation of application No. 12/001,644, filed on Dec. 11, 2007, now Pat. No. 8,481,449.

(60) Provisional application No. 60/999,057, filed on Oct. 15, 2007.

(51) Int. Cl.

| | | |
|---|---|---|
| *B01J 37/04* | (2006.01) | |
| *B01J 21/08* | (2006.01) | |
| *B01J 21/04* | (2006.01) | |
| *B01J 23/10* | (2006.01) | |
| *B01J 21/06* | (2006.01) | |
| *B01J 23/02* | (2006.01) | |
| *B01J 31/02* | (2006.01) | |
| *B01J 8/00* | (2006.01) | |
| *B01J 23/83* | (2006.01) | |
| *B01J 27/02* | (2006.01) | |
| *B01J 27/14* | (2006.01) | |
| *B01J 27/20* | (2006.01) | |
| *B01J 27/24* | (2006.01) | |
| *B01J 37/34* | (2006.01) | |
| *B01J 23/40* | (2006.01) | |
| *B01J 23/58* | (2006.01) | |
| *B01J 23/63* | (2006.01) | |
| *B01J 35/00* | (2006.01) | |
| *B01J 23/42* | (2006.01) | |
| *C07C 5/10* | (2006.01) | |
| *B01J 23/00* | (2006.01) | |
| *B01J 35/02* | (2006.01) | |
| *B01J 23/44* | (2006.01) | |
| B82Y 40/00 | (2011.01) | |
| *B01J 37/02* | (2006.01) | |

(52) U.S. Cl.
CPC ............ *B01J 21/066* (2013.01); *B01J 21/08* (2013.01); *B01J 23/00* (2013.01); *B01J 23/02* (2013.01); *B01J 23/10* (2013.01); *B01J 23/40* (2013.01); *B01J 23/42* (2013.01); *B01J 23/44* (2013.01); *B01J 23/58* (2013.01); *B01J 23/63* (2013.01); *B01J 23/83* (2013.01); *B01J 27/02* (2013.01); *B01J 27/14* (2013.01); *B01J 27/20* (2013.01); *B01J 27/24* (2013.01); *B01J 31/02* (2013.01); *B01J 35/006* (2013.01); *B01J 35/0006* (2013.01); *B01J 35/0013* (2013.01); *B01J 35/0066* (2013.01); *B01J 35/023* (2013.01); *B01J 37/0211* (2013.01); *B01J 37/04* (2013.01); *B01J 37/08* (2013.01); *B01J 37/349* (2013.01); *C07C 5/10* (2013.01); *B01J 37/0203* (2013.01); *B01J 37/0219* (2013.01); *B82Y 40/00* (2013.01); *C07C 2101/14* (2013.01); *C07C 2521/04* (2013.01); *C07C 2523/42* (2013.01); *Y02P 20/52* (2015.11); *Y10S 977/892* (2013.01); *Y10T 428/2982* (2015.01); *Y10T 428/2991* (2015.01)

(56) References Cited

U.S. PATENT DOCUMENTS

| | | |
|---|---|---|
| 2,284,554 A | 5/1942 | Beyerstedt |
| 2,419,042 A | 4/1947 | Todd |
| 2,519,531 A | 8/1950 | Worn |
| 2,562,753 A | 7/1951 | Trost |
| 2,689,780 A | 9/1954 | Rice |
| 3,001,402 A | 9/1961 | Koblin |
| 3,042,511 A | 7/1962 | Reding, Jr. |
| 3,067,025 A | 12/1962 | Chisholm |
| 3,108,006 A | 10/1963 | Kenedi et al. |
| 3,145,287 A | 8/1964 | Siebein et al. |
| 3,178,121 A | 4/1965 | Wallace, Jr. |
| 3,179,782 A | 4/1965 | Matvay |
| 3,181,947 A | 5/1965 | Vordahl |
| 3,235,700 A | 2/1966 | Mondain-Monval et al. |
| 3,290,723 A | 12/1966 | Jaques et al. |
| 3,309,873 A | 3/1967 | Cann |
| 3,313,908 A | 4/1967 | Unger et al. |
| 3,387,110 A | 6/1968 | Wendler et al. |
| 3,401,465 A | 9/1968 | Larwill |
| 3,450,926 A | 6/1969 | Kieman |
| 3,457,788 A | 7/1969 | Miyajima |
| 3,520,656 A | 7/1970 | Yates et al. |
| 3,537,513 A | 11/1970 | Austin |
| 3,552,653 A | 1/1971 | Inoue |
| 3,589,351 A | 6/1971 | Shoupp et al. |
| 3,617,358 A | 11/1971 | Dittrich |
| 3,667,111 A | 6/1972 | Chartet |
| 3,676,638 A | 7/1972 | Stand |
| 3,730,827 A | 5/1973 | Matchen et al. |
| 3,741,001 A | 6/1973 | Fletcher et al. |
| 3,743,708 A | 7/1973 | Chase et al. |
| 3,752,172 A | 8/1973 | Cohen et al. |
| 3,761,360 A | 9/1973 | Auvl et al. |
| 3,774,442 A | 11/1973 | Gustaysson |
| 3,804,034 A | 4/1974 | Stiglich, Jr. |
| 3,817,711 A | 6/1974 | Kugler et al. |
| 3,830,756 A | 8/1974 | Sanchez et al. |
| 3,857,744 A | 12/1974 | Moss |
| 3,871,448 A | 3/1975 | Vann et al. |
| 3,892,882 A | 7/1975 | Guest et al. |
| 3,914,573 A | 10/1975 | Muehlberger |
| 3,959,094 A | 5/1976 | Steinberg |
| 3,959,420 A | 5/1976 | Geddes et al. |
| 3,969,482 A | 7/1976 | Teller |
| 4,006,340 A | 2/1977 | Gorinas |
| 4,008,620 A | 2/1977 | Narato et al. |
| 4,018,388 A | 4/1977 | Andrews |
| 4,021,021 A | 5/1977 | Hall et al. |
| 4,127,760 A | 11/1978 | Meyer et al. |
| 4,139,497 A | 2/1979 | Castor et al. |
| 4,146,654 A | 3/1979 | Guyonnet |
| 4,157,316 A | 6/1979 | Thompson et al. |
| 4,171,288 A | 10/1979 | Keith et al. |
| 4,174,298 A | 11/1979 | Antos |
| 4,189,925 A | 2/1980 | Long |
| 4,227,928 A | 10/1980 | Wang |
| 4,248,387 A | 2/1981 | Andrews |
| 4,252,843 A | 2/1981 | Dorer et al. |
| 4,253,917 A | 3/1981 | Wang |
| 4,260,649 A | 4/1981 | Dension et al. |
| 4,284,609 A | 8/1981 | deVries |
| 4,315,874 A | 2/1982 | Ushida et al. |
| 4,326,492 A | 4/1982 | Leibrand, Sr. et al. |
| 4,335,080 A | 6/1982 | Davis et al. |
| 4,344,779 A | 8/1982 | Isserlis |
| 4,369,167 A | 1/1983 | Weir |
| 4,388,274 A | 6/1983 | Rourke et al. |
| 4,419,331 A | 12/1983 | Montalvo |
| 4,431,750 A | 2/1984 | McGinnis et al. |
| 4,436,075 A | 3/1984 | Campbell et al. |
| 4,440,733 A | 4/1984 | Lawson et al. |
| 4,458,138 A | 7/1984 | Adrian et al. |
| 4,459,327 A | 7/1984 | Wang |
| 4,505,945 A | 3/1985 | Dubust et al. |
| 4,506,136 A | 3/1985 | Smyth et al. |
| 4,513,149 A | 4/1985 | Gray et al. |
| 4,523,981 A | 6/1985 | Ang et al. |
| 4,545,872 A | 10/1985 | Sammells et al. |
| RE32,244 E | 9/1986 | Andersen |
| 4,609,441 A | 9/1986 | Frese, Jr. et al. |
| 4,610,857 A | 9/1986 | Ogawa et al. |
| 4,616,779 A | 10/1986 | Serrano et al. |
| 4,642,207 A | 2/1987 | Uda et al. |
| 4,665,296 A | 5/1987 | Iwata et al. |
| 4,723,589 A | 2/1988 | Iyer et al. |
| 4,731,517 A | 3/1988 | Cheney |
| 4,751,021 A | 6/1988 | Mollon et al. |

(56) References Cited

U.S. PATENT DOCUMENTS

| | | |
|---|---|---|
| 4,764,283 A | 8/1988 | Ashbrook et al. |
| 4,765,805 A | 8/1988 | Wahl et al. |
| 4,780,591 A | 10/1988 | Bernecki et al. |
| 4,824,624 A | 4/1989 | Palicka et al. |
| 4,836,084 A | 6/1989 | Vogelesang et al. |
| 4,855,505 A | 8/1989 | Koll |
| 4,866,240 A | 9/1989 | Webber |
| 4,869,936 A | 9/1989 | Moskowitz et al. |
| 4,877,937 A | 10/1989 | Müller |
| 4,885,038 A | 12/1989 | Anderson et al. |
| 4,902,870 A | 2/1990 | Frind et al. |
| 4,916,107 A | 4/1990 | Brand et al. |
| 4,921,586 A | 5/1990 | Molter |
| 4,970,364 A | 11/1990 | Müller |
| 4,982,050 A | 1/1991 | Gammie et al. |
| 4,983,555 A | 1/1991 | Roy et al. |
| 4,987,033 A | 1/1991 | Abkowitz et al. |
| 5,006,163 A | 4/1991 | Benn et al. |
| 5,013,883 A | 5/1991 | Fuimefreddo et al. |
| 5,015,863 A | 5/1991 | Takeshima et al. |
| 5,041,713 A | 8/1991 | Weidman |
| 5,043,548 A | 8/1991 | Whitney et al. |
| 5,070,064 A | 12/1991 | Hsu et al. |
| 5,073,193 A | 12/1991 | Chaklader et al. |
| 5,133,190 A | 7/1992 | Abdelmalek |
| 5,151,296 A | 9/1992 | Tokunaga |
| 5,157,007 A | 10/1992 | Domesle et al. |
| 5,187,140 A | 2/1993 | Thorsteinson et al. |
| 5,192,130 A | 3/1993 | Endo et al. |
| 5,217,746 A | 6/1993 | Lenling et al. |
| 5,225,656 A | 7/1993 | Frind |
| 5,230,844 A | 7/1993 | Macaire et al. |
| 5,233,153 A | 8/1993 | Coats |
| 5,243,169 A | 9/1993 | Tateno et al. |
| 5,260,241 A | 11/1993 | Addiego et al. |
| 5,269,848 A | 12/1993 | Nakagawa |
| 5,276,693 A | 1/1994 | Long et al. |
| 5,280,757 A | 1/1994 | Carter et al. |
| 5,294,242 A | 3/1994 | Zurecki et al. |
| 5,330,945 A | 7/1994 | Beckmeyer et al. |
| 5,338,716 A | 8/1994 | Triplett et al. |
| 5,357,075 A | 10/1994 | Muehlberger |
| 5,369,241 A | 11/1994 | Taylor et al. |
| 5,371,049 A | 12/1994 | Moffett et al. |
| 5,372,629 A | 12/1994 | Anderson et al. |
| 5,392,797 A | 2/1995 | Welch |
| 5,408,066 A | 4/1995 | Trapani et al. |
| 5,436,080 A | 7/1995 | Inoue et al. |
| 5,439,865 A | 8/1995 | Abe et al. |
| 5,442,153 A | 8/1995 | Marantz et al. |
| 5,452,854 A | 9/1995 | Keller |
| 5,460,701 A | 10/1995 | Parker et al. |
| 5,464,458 A | 11/1995 | Yamamoto |
| 5,485,941 A | 1/1996 | Guyomard et al. |
| 5,486,675 A | 1/1996 | Taylor et al. |
| 5,487,916 A | 1/1996 | Christensen |
| 5,489,449 A | 2/1996 | Umeya et al. |
| 5,510,086 A | 4/1996 | Hemingway et al. |
| 5,534,149 A | 7/1996 | Birkenbeil et al. |
| 5,534,270 A | 7/1996 | De Castro |
| 5,543,173 A | 8/1996 | Horn, Jr. et al. |
| 5,553,507 A | 9/1996 | Basch et al. |
| 5,558,771 A | 9/1996 | Hagen et al. |
| 5,562,966 A | 10/1996 | Clarke et al. |
| 5,582,807 A | 12/1996 | Liao et al. |
| 5,596,973 A | 1/1997 | Grice |
| 5,611,896 A | 3/1997 | Swanepoel et al. |
| 5,630,322 A | 5/1997 | Heilmann et al. |
| 5,652,304 A | 7/1997 | Calderon et al. |
| 5,676,912 A | 10/1997 | Sharma et al. |
| 5,714,644 A | 2/1998 | Irgang et al. |
| 5,723,027 A | 3/1998 | Serole |
| 5,723,187 A | 3/1998 | Popoola et al. |
| 5,726,414 A | 3/1998 | Kitahashi et al. |
| 5,726,415 A | 3/1998 | Luo et al. |
| 5,733,662 A | 3/1998 | Bogachek |
| 5,749,938 A | 5/1998 | Coombs |
| 5,776,359 A | 7/1998 | Schultz et al. |
| 5,788,738 A | 8/1998 | Pirzada et al. |
| 5,804,155 A | 9/1998 | Farrauto et al. |
| 5,811,187 A | 9/1998 | Anderson et al. |
| 5,837,959 A | 11/1998 | Muehlberger et al. |
| 5,851,507 A | 12/1998 | Pirzada et al. |
| 5,853,815 A | 12/1998 | Muehlberger |
| 5,858,470 A | 1/1999 | Bernecki et al. |
| 5,884,473 A | 3/1999 | Noda et al. |
| 5,905,000 A | 5/1999 | Yadav et al. |
| 5,928,806 A | 7/1999 | Olah et al. |
| 5,935,293 A | 8/1999 | Detering et al. |
| 5,973,289 A | 10/1999 | Read et al. |
| 5,989,648 A | 11/1999 | Phillips |
| 5,993,967 A | 11/1999 | Brotzman, Jr. et al. |
| 5,993,988 A | 11/1999 | Ohara et al. |
| 6,001,426 A | 12/1999 | Witherspoon et al. |
| 6,004,620 A | 12/1999 | Camm |
| 6,012,647 A | 1/2000 | Ruta et al. |
| 6,033,781 A | 3/2000 | Brotzman, Jr. et al. |
| 6,045,765 A | 4/2000 | Nakatsuji et al. |
| 6,059,853 A | 5/2000 | Coombs |
| 6,066,587 A | 5/2000 | Kurokawa et al. |
| 6,084,197 A | 7/2000 | Fusaro, Jr. |
| 6,093,306 A | 7/2000 | Hanrahan et al. |
| 6,093,378 A | 7/2000 | Deeba et al. |
| 6,102,106 A | 8/2000 | Manning et al. |
| 6,117,376 A | 9/2000 | Merkel |
| 6,139,813 A | 10/2000 | Narula et al. |
| 6,140,539 A | 10/2000 | Sander et al. |
| 6,168,694 B1 | 1/2001 | Huang et al. |
| 6,190,627 B1 | 2/2001 | Hoke et al. |
| 6,213,049 B1 | 4/2001 | Yang |
| 6,214,195 B1 | 4/2001 | Yadav et al. |
| 6,228,904 B1 | 5/2001 | Yadav et al. |
| 6,231,792 B1 | 5/2001 | Overbeek et al. |
| 6,254,940 B1 | 7/2001 | Pratsinis et al. |
| 6,261,484 B1 | 7/2001 | Phillips et al. |
| 6,267,864 B1 | 7/2001 | Yadav et al. |
| 6,322,756 B1 | 11/2001 | Arno et al. |
| 6,342,465 B1 | 1/2002 | Klein et al. |
| 6,344,271 B1 | 2/2002 | Yadav et al. |
| 6,362,449 B1 | 3/2002 | Hadidi et al. |
| 6,365,016 B1 | 4/2002 | Iacovangelo et al. |
| 6,379,419 B1 | 4/2002 | Celik et al. |
| 6,387,560 B1 | 5/2002 | Yadav et al. |
| 6,395,214 B1 | 5/2002 | Kear et al. |
| 6,398,843 B1 | 6/2002 | Tarrant |
| 6,399,030 B1 | 6/2002 | Nolan |
| 6,409,851 B1 | 6/2002 | Sethuram et al. |
| 6,413,781 B1 | 7/2002 | Geis et al. |
| 6,413,898 B1 | 7/2002 | Faber et al. |
| 6,416,818 B1 | 7/2002 | Aikens et al. |
| RE37,853 E | 9/2002 | Detering et al. |
| 6,444,009 B1 | 9/2002 | Liu et al. |
| 6,444,298 B1 | 9/2002 | Tadokoro et al. |
| 6,475,951 B1 | 11/2002 | Domesle et al. |
| 6,488,904 B1 | 12/2002 | Cox et al. |
| 6,491,423 B1 | 12/2002 | Skibo et al. |
| 6,491,985 B2 | 12/2002 | He |
| 6,506,995 B1 | 1/2003 | Fusaro, Jr. et al. |
| 6,517,800 B1 | 2/2003 | Cheng et al. |
| 6,524,662 B2 | 2/2003 | Jang et al. |
| 6,531,704 B2 | 3/2003 | Yadav et al. |
| 6,548,445 B1 | 4/2003 | Buysch et al. |
| 6,554,609 B2 | 4/2003 | Yadav et al. |
| 6,562,304 B1 | 5/2003 | Mizrahi |
| 6,562,495 B2 | 5/2003 | Yadav et al. |
| 6,569,393 B1 | 5/2003 | Hoke et al. |
| 6,569,397 B1 | 5/2003 | Yadav et al. |
| 6,569,518 B2 | 5/2003 | Yadav et al. |
| 6,572,672 B2 | 6/2003 | Yadav et al. |
| 6,579,446 B1 | 6/2003 | Teran et al. |
| 6,596,187 B2 | 7/2003 | Coll et al. |
| 6,603,038 B1 | 8/2003 | Hagemeyer et al. |
| 6,607,821 B2 | 8/2003 | Yadav et al. |
| 6,610,355 B2 | 8/2003 | Yadav et al. |

(56) References Cited

U.S. PATENT DOCUMENTS

| | | |
|---|---|---|
| 6,623,559 B2 | 9/2003 | Huang |
| 6,635,357 B2 | 10/2003 | Moxson et al. |
| 6,641,775 B2 | 11/2003 | Vigliotti et al. |
| 6,652,822 B2 | 11/2003 | Phillips et al. |
| 6,652,967 B2 | 11/2003 | Yadav et al. |
| 6,669,823 B1 | 12/2003 | Sarkas et al. |
| 6,682,002 B2 | 1/2004 | Kyotani |
| 6,689,192 B1 | 2/2004 | Phillips et al. |
| 6,699,398 B1 | 3/2004 | Kim |
| 6,706,097 B2 | 3/2004 | Zornes |
| 6,706,660 B2 | 3/2004 | Park |
| 6,710,207 B2 | 3/2004 | Bogan, Jr. et al. |
| 6,713,176 B2 | 3/2004 | Yadav et al. |
| 6,716,525 B1 | 4/2004 | Yadav et al. |
| 6,744,006 B2 | 6/2004 | Johnson et al. |
| 6,746,791 B2 | 6/2004 | Yadav et al. |
| 6,772,584 B2 | 8/2004 | Chun et al. |
| 6,780,350 B1 | 8/2004 | Kodas et al. |
| 6,786,950 B2 | 9/2004 | Yadav et al. |
| 6,813,931 B2 | 11/2004 | Yadav et al. |
| 6,817,388 B2 | 11/2004 | Tsangaris et al. |
| 6,832,735 B2 | 12/2004 | Yadav et al. |
| 6,838,072 B1 | 1/2005 | Kong et al. |
| 6,841,509 B1 | 1/2005 | Hwang et al. |
| 6,855,410 B2 | 2/2005 | Buckley |
| 6,855,426 B2 | 2/2005 | Yadav |
| 6,855,749 B1 | 2/2005 | Yadav et al. |
| 6,858,170 B2 | 2/2005 | Van Thillo et al. |
| 6,886,545 B1 | 5/2005 | Holm |
| 6,891,319 B2 | 5/2005 | Dean et al. |
| 6,896,958 B1 | 5/2005 | Cayton et al. |
| 6,902,699 B2 | 6/2005 | Fritzemeier et al. |
| 6,916,872 B2 | 7/2005 | Yadav et al. |
| 6,919,065 B2 | 7/2005 | Zhou et al. |
| 6,919,527 B2 | 7/2005 | Boulos et al. |
| 6,933,331 B2 | 8/2005 | Yadav et al. |
| 6,972,115 B1 | 12/2005 | Ballard |
| 6,986,877 B2 | 1/2006 | Takikawa et al. |
| 6,994,837 B2 | 2/2006 | Boulos et al. |
| 7,007,872 B2 | 3/2006 | Yadav et al. |
| 7,022,305 B2 | 4/2006 | Drumm et al. |
| 7,052,777 B2 | 5/2006 | Brotzman, Jr. et al. |
| 7,066,976 B2 | 6/2006 | Hampden-Smith et al. |
| 7,073,559 B2 | 7/2006 | O'Larey et al. |
| 7,074,364 B2 | 7/2006 | Jähn et al. |
| 7,081,267 B2 | 7/2006 | Yadav |
| 7,094,370 B2 | 8/2006 | Kodas et al. |
| 7,101,819 B2 | 9/2006 | Rosenflanz et al. |
| 7,147,544 B2 | 12/2006 | Rosenflanz |
| 7,147,894 B2 | 12/2006 | Zhou et al. |
| 7,166,198 B2 | 1/2007 | Van Der Walt et al. |
| 7,166,663 B2 | 1/2007 | Cayton et al. |
| 7,172,649 B2 | 2/2007 | Conrad et al. |
| 7,172,790 B2 | 2/2007 | Koulik et al. |
| 7,178,747 B2 | 2/2007 | Yadav et al. |
| 7,208,126 B2 | 4/2007 | Musick et al. |
| 7,211,236 B2 | 5/2007 | Stark et al. |
| 7,217,407 B2 | 5/2007 | Zhang |
| 7,220,398 B2 | 5/2007 | Sutorik et al. |
| 7,255,498 B2 | 8/2007 | Bush et al. |
| 7,265,076 B2 | 9/2007 | Taguchi et al. |
| 7,282,167 B2 | 10/2007 | Carpenter |
| 7,307,195 B2 | 12/2007 | Polverejan et al. |
| 7,323,655 B2 | 1/2008 | Kim |
| 7,384,447 B2 | 6/2008 | Kodas et al. |
| 7,402,899 B1 | 7/2008 | Whiting et al. |
| 7,417,008 B2 | 8/2008 | Richards et al. |
| 7,494,527 B2 | 2/2009 | Jurewicz et al. |
| 7,507,495 B2 | 3/2009 | Wang et al. |
| 7,517,826 B2 | 4/2009 | Fujdala et al. |
| 7,534,738 B2 | 5/2009 | Fujdala et al. |
| 7,541,012 B2 | 6/2009 | Yeung et al. |
| 7,541,310 B2 | 6/2009 | Espinoza et al. |
| 7,557,324 B2 | 7/2009 | Nylen et al. |
| 7,572,315 B2 | 8/2009 | Boulos et al. |
| 7,576,029 B2 | 8/2009 | Saito et al. |
| 7,576,031 B2 | 8/2009 | Beutel et al. |
| 7,601,294 B2 | 10/2009 | Ripley et al. |
| 7,604,843 B1 | 10/2009 | Robinson et al. |
| 7,611,686 B2 | 11/2009 | Alekseeva et al. |
| 7,615,097 B2 | 11/2009 | McKechnie et al. |
| 7,618,919 B2 | 11/2009 | Shimazu et al. |
| 7,622,693 B2 | 11/2009 | Foret |
| 7,632,775 B2 | 12/2009 | Zhou et al. |
| 7,635,218 B1 | 12/2009 | Lott |
| 7,674,744 B2 | 3/2010 | Shiratori et al. |
| 7,678,419 B2 | 3/2010 | Kevwitch et al. |
| 7,704,369 B2 | 4/2010 | Olah et al. |
| 7,709,411 B2 | 5/2010 | Zhou et al. |
| 7,709,414 B2 | 5/2010 | Fujdala et al. |
| 7,745,367 B2 | 6/2010 | Fujdala et al. |
| 7,750,265 B2 | 7/2010 | Belashchenko |
| 7,759,279 B2 | 7/2010 | Shiratori et al. |
| 7,759,281 B2 | 7/2010 | Kezuka et al. |
| 7,803,210 B2 | 9/2010 | Sekine et al. |
| 7,842,515 B2 | 11/2010 | Zou et al. |
| 7,851,405 B2 | 12/2010 | Wakamatsu et al. |
| 7,874,239 B2 | 1/2011 | Howland |
| 7,875,573 B2 | 1/2011 | Beutel et al. |
| 7,897,127 B2 | 3/2011 | Layman et al. |
| 7,897,536 B2 | 3/2011 | Saito et al. |
| 7,902,104 B2 | 3/2011 | Kalck |
| 7,905,942 B1 | 3/2011 | Layman |
| 7,935,655 B2 | 5/2011 | Tolmachev |
| 7,951,428 B2 | 5/2011 | Hoerr et al. |
| 8,003,020 B2 | 8/2011 | Jankowiak et al. |
| 8,051,724 B1 | 11/2011 | Layman et al. |
| 8,076,258 B1 | 12/2011 | Biberger |
| 8,080,494 B2 | 12/2011 | Yasuda et al. |
| 8,089,495 B2 | 1/2012 | Keller |
| 8,129,654 B2 | 3/2012 | Lee et al. |
| 8,142,619 B2 | 3/2012 | Layman et al. |
| 8,168,561 B2 | 5/2012 | Virkar |
| 8,173,572 B2 | 5/2012 | Feaviour |
| 8,176,830 B1 | 5/2012 | Tan |
| 8,211,392 B2 | 7/2012 | Grubert et al. |
| 8,258,070 B2 | 9/2012 | Fujdala et al. |
| 8,278,240 B2 | 10/2012 | Tange et al. |
| 8,294,060 B2 | 10/2012 | Mohanty et al. |
| 8,309,489 B2 | 11/2012 | Roldan Cuenya et al. |
| 8,349,761 B2 | 1/2013 | Xia et al. |
| 8,404,611 B2 | 3/2013 | Nakamura et al. |
| 8,470,112 B1 | 6/2013 | Biberger |
| 8,481,449 B1 | 7/2013 | Biberger et al. |
| 8,507,401 B1 | 8/2013 | Biberger et al. |
| 8,507,402 B1 | 8/2013 | Biberger et al. |
| 8,518,846 B2 | 8/2013 | Uchikawa et al. |
| 8,524,631 B2 | 9/2013 | Biberger |
| 8,545,652 B1 | 10/2013 | Biberger |
| 8,557,727 B2 | 10/2013 | Yin et al. |
| 8,574,408 B2 | 11/2013 | Layman |
| 8,574,520 B2 | 11/2013 | Koplin et al. |
| 8,575,059 B1 * | 11/2013 | Biberger ............... B01J 37/08 427/201 |
| 8,604,398 B1 | 12/2013 | Layman |
| 8,652,992 B2 | 2/2014 | Yin et al. |
| 8,668,803 B1 | 3/2014 | Biberger |
| 8,669,202 B2 | 3/2014 | van den Hoek et al. |
| 8,679,433 B2 | 3/2014 | Yin et al. |
| 8,821,786 B1 | 9/2014 | Biberger |
| 8,828,328 B1 | 9/2014 | Leamon et al. |
| 8,859,035 B1 | 10/2014 | Leamon |
| 8,877,357 B1 | 11/2014 | Biberger |
| 8,893,651 B1 | 11/2014 | Biberger et al. |
| 8,906,498 B1 | 12/2014 | Biberger |
| 8,927,403 B2 | 1/2015 | Huotari et al. |
| 8,932,514 B1 | 1/2015 | Yin et al. |
| 8,969,237 B2 | 3/2015 | Yin et al. |
| 8,992,820 B1 | 3/2015 | Yin et al. |
| 9,023,754 B2 | 5/2015 | Biberger |
| 9,039,916 B1 | 5/2015 | Lehman, Jr. |
| 9,089,840 B2 * | 7/2015 | Biberger ............... B01J 37/08 |
| 9,090,475 B1 | 7/2015 | Lehman, Jr. |
| 9,119,309 B1 | 8/2015 | Lehman, Jr. |

(56) References Cited

U.S. PATENT DOCUMENTS

| | | |
|---|---|---|
| 9,126,191 B2 | 9/2015 | Yin et al. |
| 9,132,404 B2 | 9/2015 | Layman |
| 9,149,797 B2 | 10/2015 | Leamon |
| 9,156,025 B2 | 10/2015 | Qi et al. |
| 9,180,423 B2 | 11/2015 | Biberger et al. |
| 9,186,663 B2 * | 11/2015 | Biberger ................ B01J 37/08 |
| 9,216,398 B2 | 12/2015 | Biberger et al. |
| 9,216,406 B2 | 12/2015 | Van Den Hoek et al. |
| 9,308,524 B2 | 4/2016 | Yin et al. |
| 9,332,636 B2 | 5/2016 | Biberger |
| 2001/0004009 A1 | 6/2001 | MacKelvie |
| 2001/0042802 A1 | 11/2001 | Youds |
| 2001/0055554 A1 | 12/2001 | Hoke et al. |
| 2002/0018815 A1 | 2/2002 | Sievers et al. |
| 2002/0068026 A1 | 6/2002 | Murrell et al. |
| 2002/0071800 A1 | 6/2002 | Hoke et al. |
| 2002/0079620 A1 | 6/2002 | DuBuis et al. |
| 2002/0100751 A1 | 8/2002 | Carr |
| 2002/0102674 A1 | 8/2002 | Anderson |
| 2002/0131914 A1 | 9/2002 | Sung |
| 2002/0143417 A1 | 10/2002 | Ito et al. |
| 2002/0168466 A1 | 11/2002 | Tapphorn et al. |
| 2002/0182735 A1 | 12/2002 | Kibby et al. |
| 2002/0183191 A1 | 12/2002 | Faber et al. |
| 2002/0192129 A1 | 12/2002 | Shamouilian et al. |
| 2003/0036786 A1 | 2/2003 | Duren et al. |
| 2003/0042232 A1 | 3/2003 | Shimazu |
| 2003/0047617 A1 | 3/2003 | Shanmugham et al. |
| 2003/0066800 A1 | 4/2003 | Saim et al. |
| 2003/0085663 A1 | 5/2003 | Horsky |
| 2003/0102099 A1 | 6/2003 | Yadav et al. |
| 2003/0108459 A1 | 6/2003 | Wu et al. |
| 2003/0110931 A1 | 6/2003 | Aghajanian et al. |
| 2003/0129098 A1 | 7/2003 | Endo et al. |
| 2003/0139288 A1 | 7/2003 | Cai et al. |
| 2003/0143153 A1 | 7/2003 | Boulos et al. |
| 2003/0172772 A1 | 9/2003 | Sethuram et al. |
| 2003/0223546 A1 | 12/2003 | McGregor et al. |
| 2004/0007092 A1 | 1/2004 | Yoshimura |
| 2004/0009118 A1 | 1/2004 | Phillips et al. |
| 2004/0023302 A1 | 2/2004 | Archibald et al. |
| 2004/0023453 A1 | 2/2004 | Xu et al. |
| 2004/0065170 A1 | 4/2004 | Wu et al. |
| 2004/0077494 A1 | 4/2004 | LaBarge et al. |
| 2004/0103751 A1 | 6/2004 | Joseph et al. |
| 2004/0109523 A1 | 6/2004 | Singh et al. |
| 2004/0119064 A1 | 6/2004 | Narayan et al. |
| 2004/0127586 A1 | 7/2004 | Jin et al. |
| 2004/0129222 A1 | 7/2004 | Nylen et al. |
| 2004/0166036 A1 | 8/2004 | Chen et al. |
| 2004/0167009 A1 | 8/2004 | Kuntz et al. |
| 2004/0176246 A1 | 9/2004 | Shirk et al. |
| 2004/0178530 A1 | 9/2004 | Yadav |
| 2004/0208805 A1 | 10/2004 | Fincke et al. |
| 2004/0213998 A1 | 10/2004 | Hearley et al. |
| 2004/0235657 A1 | 11/2004 | Xiao et al. |
| 2004/0238345 A1 | 12/2004 | Koulik et al. |
| 2004/0251017 A1 | 12/2004 | Pillion et al. |
| 2004/0251241 A1 | 12/2004 | Blutke et al. |
| 2005/0000321 A1 | 1/2005 | O'Larey et al. |
| 2005/0000950 A1 | 1/2005 | Schroder et al. |
| 2005/0058797 A1 | 3/2005 | Sen et al. |
| 2005/0066805 A1 | 3/2005 | Park et al. |
| 2005/0070431 A1 | 3/2005 | Alvin et al. |
| 2005/0077034 A1 | 4/2005 | King |
| 2005/0097988 A1 | 5/2005 | Kodas et al. |
| 2005/0106865 A1 | 5/2005 | Chung et al. |
| 2005/0119398 A1 | 6/2005 | Zhang |
| 2005/0133121 A1 | 6/2005 | Subramanian et al. |
| 2005/0153069 A1 | 7/2005 | Tapphorn et al. |
| 2005/0163673 A1 | 7/2005 | Johnson et al. |
| 2005/0199739 A1 | 9/2005 | Kuroda et al. |
| 2005/0211018 A1 | 9/2005 | Jurewicz et al. |
| 2005/0220695 A1 | 10/2005 | Abatzoglou et al. |
| 2005/0227864 A1 | 10/2005 | Sutorik et al. |
| 2005/0233380 A1 | 10/2005 | Pesiri et al. |
| 2005/0240069 A1 | 10/2005 | Polverejan et al. |
| 2005/0258766 A1 | 11/2005 | Kim |
| 2005/0274646 A1 | 12/2005 | Lawson et al. |
| 2005/0275143 A1 | 12/2005 | Toth |
| 2006/0043651 A1 | 3/2006 | Yamamoto et al. |
| 2006/0051505 A1 | 3/2006 | Kortshagen et al. |
| 2006/0068989 A1 | 3/2006 | Ninomiya et al. |
| 2006/0094595 A1 | 5/2006 | Labarge |
| 2006/0096393 A1 | 5/2006 | Pesiri |
| 2006/0105910 A1 | 5/2006 | Zhou et al. |
| 2006/0108332 A1 | 5/2006 | Belashchenko |
| 2006/0153728 A1 | 7/2006 | Schoenung et al. |
| 2006/0153765 A1 | 7/2006 | Pham-Huu et al. |
| 2006/0159596 A1 | 7/2006 | De La Veaux et al. |
| 2006/0166809 A1 | 7/2006 | Malek et al. |
| 2006/0211569 A1 | 9/2006 | Dang et al. |
| 2006/0213326 A1 | 9/2006 | Gollob et al. |
| 2006/0222777 A1 | 10/2006 | Skoog et al. |
| 2006/0222780 A1 | 10/2006 | Gurevich et al. |
| 2006/0231525 A1 | 10/2006 | Asakawa et al. |
| 2007/0009752 A1 | 1/2007 | Lefebvre et al. |
| 2007/0014919 A1 | 1/2007 | Hamalainen et al. |
| 2007/0020167 A1 | 1/2007 | Han et al. |
| 2007/0044513 A1 | 3/2007 | Kear et al. |
| 2007/0048206 A1 | 3/2007 | Hung et al. |
| 2007/0049484 A1 | 3/2007 | Kear et al. |
| 2007/0063364 A1 | 3/2007 | Hsiao et al. |
| 2007/0084308 A1 | 4/2007 | Nakamura et al. |
| 2007/0084834 A1 | 4/2007 | Hanus et al. |
| 2007/0087934 A1 | 4/2007 | Martens et al. |
| 2007/0092768 A1 | 4/2007 | Lee et al. |
| 2007/0153390 A1 | 7/2007 | Nakamura et al. |
| 2007/0161506 A1 | 7/2007 | Saito et al. |
| 2007/0163385 A1 | 7/2007 | Takahashi et al. |
| 2007/0172721 A1 | 7/2007 | Pak et al. |
| 2007/0173403 A1 | 7/2007 | Koike et al. |
| 2007/0178673 A1 | 8/2007 | Gole et al. |
| 2007/0221404 A1 | 9/2007 | Das et al. |
| 2007/0253874 A1 | 11/2007 | Foret |
| 2007/0259768 A1 | 11/2007 | Kear et al. |
| 2007/0266825 A1 | 11/2007 | Ripley et al. |
| 2007/0292321 A1 | 12/2007 | Plischke et al. |
| 2008/0006954 A1 | 1/2008 | Yubuta et al. |
| 2008/0026041 A1 | 1/2008 | Tepper et al. |
| 2008/0026932 A1 | 1/2008 | Satoh et al. |
| 2008/0031806 A1 | 2/2008 | Gavenonis et al. |
| 2008/0038578 A1 | 2/2008 | Li |
| 2008/0045405 A1 | 2/2008 | Beutel et al. |
| 2008/0047261 A1 | 2/2008 | Han et al. |
| 2008/0056977 A1 | 3/2008 | Hung et al. |
| 2008/0057212 A1 | 3/2008 | Dorier et al. |
| 2008/0064769 A1 | 3/2008 | Sato et al. |
| 2008/0104735 A1 | 5/2008 | Howland |
| 2008/0105083 A1 | 5/2008 | Nakamura et al. |
| 2008/0107586 A1 | 5/2008 | Smalley et al. |
| 2008/0108005 A1 | 5/2008 | Carpenter |
| 2008/0116118 A1 | 5/2008 | Zhu et al. |
| 2008/0116178 A1 | 5/2008 | Weidman |
| 2008/0125308 A1 | 5/2008 | Fujdala et al. |
| 2008/0125313 A1 | 5/2008 | Fujdala et al. |
| 2008/0138651 A1 | 6/2008 | Doi et al. |
| 2008/0175936 A1 | 7/2008 | Tokita et al. |
| 2008/0187714 A1 | 8/2008 | Wakamatsu et al. |
| 2008/0202288 A1 | 8/2008 | McKechnie et al. |
| 2008/0206562 A1 | 8/2008 | Stucky et al. |
| 2008/0207858 A1 | 8/2008 | Kowaleski et al. |
| 2008/0248704 A1 | 10/2008 | Mathis et al. |
| 2008/0268270 A1 | 10/2008 | Chen et al. |
| 2008/0274344 A1 | 11/2008 | Vieth et al. |
| 2008/0277092 A1 | 11/2008 | Layman et al. |
| 2008/0277264 A1 | 11/2008 | Sprague |
| 2008/0277266 A1 | 11/2008 | Layman |
| 2008/0277267 A1 | 11/2008 | Biberger et al. |
| 2008/0277268 A1 | 11/2008 | Layman |
| 2008/0277269 A1 | 11/2008 | Layman et al. |
| 2008/0277270 A1 | 11/2008 | Biberger et al. |
| 2008/0277271 A1 | 11/2008 | Layman |
| 2008/0280049 A1 | 11/2008 | Kevwitch et al. |

(56) References Cited

U.S. PATENT DOCUMENTS

| | | |
|---|---|---|
| 2008/0280751 A1 | 11/2008 | Harutyunyan et al. |
| 2008/0280756 A1 | 11/2008 | Biberger |
| 2008/0283411 A1 | 11/2008 | Eastman et al. |
| 2008/0283498 A1 | 11/2008 | Yamazaki |
| 2008/0307960 A1 | 12/2008 | Hendrickson et al. |
| 2009/0010801 A1 | 1/2009 | Murphy et al. |
| 2009/0018008 A1 | 1/2009 | Jankowiak et al. |
| 2009/0054230 A1 | 2/2009 | Veeraraghavan et al. |
| 2009/0080592 A1 | 3/2009 | Arsenlis et al. |
| 2009/0081092 A1 | 3/2009 | Yang et al. |
| 2009/0088585 A1 | 4/2009 | Schammel et al. |
| 2009/0092887 A1 | 4/2009 | McGrath et al. |
| 2009/0098402 A1 | 4/2009 | Kang et al. |
| 2009/0114568 A1 | 5/2009 | Trevino et al. |
| 2009/0162991 A1 | 6/2009 | Beneyton et al. |
| 2009/0168506 A1 | 7/2009 | Han et al. |
| 2009/0170242 A1 | 7/2009 | Lin et al. |
| 2009/0181474 A1 | 7/2009 | Nagai |
| 2009/0200180 A1 | 8/2009 | Capote et al. |
| 2009/0208367 A1 | 8/2009 | Calio et al. |
| 2009/0209408 A1 | 8/2009 | Kitamura et al. |
| 2009/0223410 A1 | 9/2009 | Jun et al. |
| 2009/0238736 A1 | 9/2009 | Takahashi |
| 2009/0253037 A1 | 10/2009 | Park et al. |
| 2009/0274897 A1 | 11/2009 | Kaner et al. |
| 2009/0274903 A1 | 11/2009 | Addiego |
| 2009/0286899 A1 | 11/2009 | Hofmann et al. |
| 2009/0320449 A1 | 12/2009 | Beutel et al. |
| 2009/0324468 A1 | 12/2009 | Golden et al. |
| 2010/0050868 A1 | 3/2010 | Kuznicki et al. |
| 2010/0089002 A1 | 4/2010 | Merkel |
| 2010/0089742 A1 | 4/2010 | Suslov |
| 2010/0092358 A1 | 4/2010 | Koegel et al. |
| 2010/0124514 A1 | 5/2010 | Chelluri et al. |
| 2010/0166629 A1 | 7/2010 | Deeba |
| 2010/0180581 A1 | 7/2010 | Grubert et al. |
| 2010/0180582 A1 | 7/2010 | Mueller-Stach et al. |
| 2010/0180820 A1 | 7/2010 | Ishimaru et al. |
| 2010/0186375 A1 | 7/2010 | Kazi et al. |
| 2010/0240525 A1 | 9/2010 | Golden et al. |
| 2010/0260652 A1 | 10/2010 | Nakane et al. |
| 2010/0275781 A1 | 11/2010 | Tsangaris |
| 2010/0283013 A1 | 11/2010 | Sato et al. |
| 2010/0323118 A1 | 12/2010 | Mohanty et al. |
| 2011/0006463 A1 | 1/2011 | Layman |
| 2011/0030346 A1 | 2/2011 | Neubauer et al. |
| 2011/0049045 A1 | 3/2011 | Hurt et al. |
| 2011/0052467 A1 | 3/2011 | Chase et al. |
| 2011/0052698 A1 | 3/2011 | Benoit et al. |
| 2011/0143041 A1 | 6/2011 | Layman et al. |
| 2011/0143915 A1 | 6/2011 | Yin et al. |
| 2011/0143916 A1 | 6/2011 | Leamon |
| 2011/0143926 A1 | 6/2011 | Yin et al. |
| 2011/0143930 A1 | 6/2011 | Yin et al. |
| 2011/0143933 A1 | 6/2011 | Yin et al. |
| 2011/0144382 A1 | 6/2011 | Yin et al. |
| 2011/0152550 A1 | 6/2011 | Grey et al. |
| 2011/0154807 A1 | 6/2011 | Chandler et al. |
| 2011/0158871 A1 | 6/2011 | Arnold et al. |
| 2011/0174604 A1 | 7/2011 | Duesel et al. |
| 2011/0180750 A1 | 7/2011 | Kleine Jaeger et al. |
| 2011/0243808 A1 | 10/2011 | Fossey et al. |
| 2011/0245073 A1 | 10/2011 | Oljaca et al. |
| 2011/0247336 A9 | 10/2011 | Farsad et al. |
| 2011/0271658 A1 | 11/2011 | Hoyer et al. |
| 2011/0305612 A1 | 12/2011 | Müller-Stach et al. |
| 2012/0023909 A1 | 2/2012 | Lambert et al. |
| 2012/0045373 A1 | 2/2012 | Biberger |
| 2012/0063963 A1 | 3/2012 | Watanabe et al. |
| 2012/0097033 A1 | 4/2012 | Arnold et al. |
| 2012/0122660 A1 | 5/2012 | Andersen et al. |
| 2012/0124974 A1 | 5/2012 | Li et al. |
| 2012/0171098 A1 | 7/2012 | Hung et al. |
| 2012/0214666 A1 | 8/2012 | van den Hoek et al. |
| 2012/0263633 A1 | 10/2012 | Koplin et al. |
| 2012/0285548 A1 | 11/2012 | Layman et al. |
| 2012/0308467 A1 | 12/2012 | Carpenter et al. |
| 2012/0313269 A1 | 12/2012 | Kear et al. |
| 2013/0034472 A1 | 2/2013 | Cantrell et al. |
| 2013/0064750 A1 | 3/2013 | Zettl |
| 2013/0079216 A1 | 3/2013 | Biberger et al. |
| 2013/0125970 A1 | 5/2013 | Ko et al. |
| 2013/0213018 A1 | 8/2013 | Yin et al. |
| 2013/0270355 A1 | 10/2013 | Cotler et al. |
| 2013/0280528 A1 | 10/2013 | Biberger |
| 2013/0281288 A1 | 10/2013 | Biberger et al. |
| 2013/0294989 A1 | 11/2013 | Koch et al. |
| 2013/0316896 A1 | 11/2013 | Biberger |
| 2013/0331257 A1 | 12/2013 | Barcikowski et al. |
| 2013/0345047 A1 | 12/2013 | Biberger et al. |
| 2014/0018230 A1 | 1/2014 | Yin et al. |
| 2014/0120355 A1 | 5/2014 | Biberger |
| 2014/0128245 A1 | 5/2014 | Yin et al. |
| 2014/0140909 A1 | 5/2014 | Qi et al. |
| 2014/0148331 A1 | 5/2014 | Biberger et al. |
| 2014/0161693 A1 | 6/2014 | Brown et al. |
| 2014/0209451 A1 | 7/2014 | Biberger et al. |
| 2014/0228201 A1 | 8/2014 | Mendoza Goómez et al. |
| 2014/0243187 A1 | 8/2014 | Yin et al. |
| 2014/0249021 A1 | 9/2014 | van den Hoek et al. |
| 2014/0252270 A1 | 9/2014 | Lehman, Jr. |
| 2014/0263190 A1 | 9/2014 | Biberger et al. |
| 2014/0318318 A1 | 10/2014 | Layman et al. |
| 2014/0338519 A1 | 11/2014 | Biberger |
| 2015/0093312 A1 | 4/2015 | Yin et al. |
| 2015/0140317 A1 | 5/2015 | Biberger et al. |
| 2015/0141236 A1 | 5/2015 | Yin et al. |
| 2015/0165418 A1 | 6/2015 | Kearl et al. |
| 2015/0165434 A1 | 6/2015 | Yin et al. |
| 2015/0196884 A1 | 7/2015 | Layman |
| 2015/0217229 A1 | 8/2015 | Yin et al. |
| 2015/0266002 A1 | 9/2015 | Biberger et al. |
| 2015/0314260 A1 | 11/2015 | Biberger |
| 2015/0314581 A1 | 11/2015 | Biberger |
| 2015/0367331 A1 | 12/2015 | Biberger |
| 2016/0045867 A1 | 2/2016 | Kearl et al. |
| 2016/0067679 A1 | 3/2016 | Yin et al. |
| 2016/0074855 A1 | 3/2016 | Qi et al. |
| 2016/0138870 A1 | 5/2016 | Biberger et al. |
| 2016/0144352 A1 | 5/2016 | van Den Hoek et al. |

FOREIGN PATENT DOCUMENTS

| | | |
|---|---|---|
| CN | 101301610 A | 11/2008 |
| DE | 34 45 273 A1 | 6/1986 |
| EP | 0 223 104 A1 | 5/1987 |
| EP | 0 347 386 A1 | 12/1989 |
| EP | 0 385 742 A1 | 9/1990 |
| EP | 1 134 302 A1 | 9/2001 |
| EP | 1 256 378 A2 | 11/2002 |
| EP | 1 619 168 A1 | 1/2006 |
| EP | 1 721 690 A1 | 11/2006 |
| EP | 1 790 612 A1 | 5/2007 |
| EP | 1 955 765 A1 | 8/2008 |
| GB | 1 307 941 A | 2/1973 |
| JP | 30-13577 U | 9/1955 |
| JP | 47-21256 U | 2/1971 |
| JP | 49-31571 A | 3/1974 |
| JP | 51-7582 U | 7/1974 |
| JP | 52-165360 U | 6/1976 |
| JP | 56-146804 A | 11/1981 |
| JP | 58-160794 A | 9/1983 |
| JP | 59-59410 A | 4/1984 |
| JP | 61-086815 A | 5/1986 |
| JP | 61-242644 A | 10/1986 |
| JP | 62-102827 A | 5/1987 |
| JP | 63-214342 A | 9/1988 |
| JP | 1-164795 A | 6/1989 |
| JP | 1-275708 A | 11/1989 |
| JP | 2-6339 A | 1/1990 |
| JP | 2-160040 A | 6/1990 |
| JP | 2-203932 A | 8/1990 |
| JP | 3-226509 A | 10/1991 |
| JP | 5-193909 A | 8/1993 |

(56) References Cited

FOREIGN PATENT DOCUMENTS

| | | |
|---|---|---|
| JP | 05-228361 A | 9/1993 |
| JP | 05-324094 A | 12/1993 |
| JP | 6-91162 A | 4/1994 |
| JP | 6-93309 A | 4/1994 |
| JP | 6-135797 A | 5/1994 |
| JP | 6-172820 A | 6/1994 |
| JP | 6-272012 A | 9/1994 |
| JP | H6-065772 U | 9/1994 |
| JP | 07-031873 A | 2/1995 |
| JP | 7-20553 B2 | 3/1995 |
| JP | 7-120176 A | 5/1995 |
| JP | 7-138020 A | 5/1995 |
| JP | 7-207381 A | 8/1995 |
| JP | 07-256116 A | 10/1995 |
| JP | 8-158033 A | 6/1996 |
| JP | 8-215576 A | 8/1996 |
| JP | 8-217420 A | 8/1996 |
| JP | 9-141087 A | 6/1997 |
| JP | 10-130810 A | 5/1998 |
| JP | 10-249198 A | 9/1998 |
| JP | 11-502760 A | 3/1999 |
| JP | 11-300198 A | 11/1999 |
| JP | 2000-220978 A | 8/2000 |
| JP | 2002-88486 A | 3/2002 |
| JP | 2002-241812 A | 8/2002 |
| JP | 2002-263496 A | 9/2002 |
| JP | 2002-336688 A | 11/2002 |
| JP | 2003-126694 A | 5/2003 |
| JP | 2003-170043 A | 6/2003 |
| JP | 2003-261323 A | 9/2003 |
| JP | 2004-233007 A | 8/2004 |
| JP | 2004-249206 A | 9/2004 |
| JP | 2004-290730 A | 10/2004 |
| JP | 2005-503250 A | 2/2005 |
| JP | 2005-122621 A | 5/2005 |
| JP | 2005-218937 A | 8/2005 |
| JP | 2005-342615 A | 12/2005 |
| JP | 2006-001779 A | 1/2006 |
| JP | 2006-508885 A | 3/2006 |
| JP | 2006-87965 A | 4/2006 |
| JP | 2006-181484 A | 7/2006 |
| JP | 2006-247446 A | 9/2006 |
| JP | 2006-260385 A | 9/2006 |
| JP | 2006-272265 A | 10/2006 |
| JP | 2006-326554 A | 12/2006 |
| JP | 2007-29859 A | 2/2007 |
| JP | 2007-44585 A | 2/2007 |
| JP | 2007-46162 A | 2/2007 |
| JP | 2007-138287 A | 6/2007 |
| JP | 2007-203129 A | 8/2007 |
| JP | 2007-222732 A | 9/2007 |
| JP | 2007-253037 A | 10/2007 |
| JP | 2009-254929 | 11/2009 |
| JP | 2009-279544 A | 12/2009 |
| SU | 493241 A | 3/1976 |
| TW | 200611449 | 4/2006 |
| TW | 201023207 | 6/2010 |
| WO | WO-96/28577 A1 | 9/1996 |
| WO | WO-00/16882 | 3/2000 |
| WO | WO-00/72965 A1 | 12/2000 |
| WO | WO-02/092503 A1 | 11/2002 |
| WO | WO-03/094195 A1 | 11/2003 |
| WO | WO-2004/052778 A2 | 6/2004 |
| WO | WO-2005/063390 A1 | 7/2005 |
| WO | WO-2006/079213 A1 | 8/2006 |
| WO | WO-2006/096205 A2 | 9/2006 |
| WO | WO-2007/144447 A1 | 12/2007 |
| WO | WO-2008/088649 A1 | 7/2008 |
| WO | WO-2008/092478 A1 | 8/2008 |
| WO | WO-2008/130451 A2 | 10/2008 |
| WO | WO-2008/130451 A3 | 10/2008 |
| WO | WO-2009/017479 A1 | 2/2009 |
| WO | WO-2011/081833 A1 | 7/2011 |
| WO | WO-2011/081834 A1 | 7/2011 |
| WO | WO-2012/028695 A2 | 3/2012 |
| WO | WO-2013/028575 A1 | 2/2013 |
| WO | WO-2013/093597 A2 | 6/2013 |
| WO | WO-2013/151557 A1 | 10/2013 |
| WO | WO-2016/033517 A1 | 3/2016 |

OTHER PUBLICATIONS

Babin, A. et al. (1985). "Solvents Used in the Arts," *Center for Safety in the Arts*: 16 pages.

Bateman, J. E. et al. (Dec. 17, 1998). "Alkylation of Porous Silicon by Direct Reaction with Alkenes and Alkynes," *Angew. Chem Int. Ed.* 37(19):2683-2685.

Birlik, I. et al. (Jun. 15, 2010). "Nanoparticle Doped YBCO Films Prepared by Chemical Solution Deposition Method," *6th Nanoscience and Nanotechnology Conference, Izmir, Turkey*: 1 page.

Büchel, R. et al. (2009). "Influence of Pt Location on $BaCO_3$ or $Al_2O_3$ During $NO_x$ Storage Reduction," *Journal of Catalysis* 261: 201-207.

Carrot, G. et al. (Sep. 17, 2002). "Surface-Initiated Ring-Opening Polymerization: A Versatile Method for Nanoparticle Ordering," *Macromolecules* 35(22):8400-8404.

Chaim, R. et al. (2009). "Densification of Nanocrystalline $Y_2O_3$ Ceramic Powder by Spark Plasma Sintering," *Journal of European Ceramic Society* 29: 91-98.

Chau, J. K. H. et al. (2005). "Microwave Plasma Synthesis of Silver Nanopowders," *Materials Letters* 59: 905-908.

Chen, H.-S. et al. (Jul. 3, 2001). "On the Photoluminescence of Si Nanoparticles," *Mater. Phys. Mech.* 4:62-66.

Chen, W.-J. et al. (Mar. 18, 2008). "Functional $Fe_3O_4/TiO_2$ Core/Shell Magnetic Nanoparticles as Photokilling Agents for Pathogenic Bacteria," *Small* 4(4): 485-491.

Cospheric LLC. (Mar. 13, 2010). "Porous Ceramics: Application for Polyethylene Microspheres," Microspheres Online, located at http://microspheres.us/microsphere-manufacturing/porous-ceramics-polyethylene-microspheres/177.html, last accessed Mar. 17, 2015, 6 pages.

Das, N. et al. (2001). "Influence of the Metal Function in the "One-Pot" Synthesis of 4-Methyl-2-Pentanone (Methyl Isobutyl Ketone) from Acetone Over Palladium Supported on Mg(Al)O Mixed Oxides Catalysts," *Catalysis Letters* 71(3-4): 181-185.

Date, A. R. et al. (1987). "The Potential of Fire Assay and Inductively Coupled Plasama Source Mass Spectrometry for the Determination of Platinum Group Elements in Geological Materials," *Analyst* 112: 1217-1222.

Faber, K. T. et al. (Sep. 1988). "Toughening by Stress-Induced Microcracking in Two-Phase Ceramics," Journal of the American Ceramic Society 71: C-399-C401.

Fauchais, P. et al. (Jun. 1989). "La Projection Par Plasma: Une Revue," *Ann. Phys. Fr.* 14(3):261-310.

Fauchais, P. et al. (Jan. 1993). "Les Dépôts Par Plasma Thermique," Revue Générale De L'Electricité, RGE, Paris, France, No. 2, pp. 7-12 (in French). (Submit with Machine translation).

Fauchais, P. et al. (Jan. 1996). "Plasma Spray: Study of the Coating Generation," *Ceramics International* 22(4):295-303.

Fojtik, A. et al. (Apr. 29, 1994). "Luminescent Colloidal Silicon Particles,"*Chemical Physics Letters* 221:363-367.

Fojtik, A. (Jan. 13, 2006). "Surface Chemistry of Luminescent Colloidal Silicon Nanoparticles," *J. Phys. Chem. B.* 110(5):1994-1998.

Gangeri, M. et al. (2009). "Fe and Pt Carbon Nanotubes for the Electrocatalytic Conversion of Carbon Dioxide to Oxygenates," *Catalysis Today* 143: 57-63.

Gutsch, A. et al. (2002). "Gas-Phase Production of Nanoparticles," *Kona* No. 20, pp. 24-37.

Han, B. Q. et al. (Jan. 2004). "Deformation Mechanisms and Ductility of Nanostructured Al Alloys", *Mat. Res. Soc. Symp. Proc.* 821:p. 9.1.1-p. 9.1.6.

Heberlein, J. (2002). "New Approaches in Thermal Plasma Technology", *Pure App. Chem.* 74(3):327-335.

Hua, F. et al. (Mar. 2006). "Organically Capped Silicon Nanoparticles With Blue Photoluminescence Prepared by Hydrosilylation Followed by Oxidation," *Langmuir* 22(9):4363-4370.

(56) References Cited

OTHER PUBLICATIONS

Ihlein, G. et al.(1998). "Ordered Porous Materials as Media for the Organization of Matter on the Nanoscale," *Applied Organometallic Chemistry* 12: 305-314.

Jensen, J. et al. (2000). "Preparation of ZnO—$Al_2O_3$ Particles in a Premixed Flame," *Journal of Nanoparticle Research* 2: 363-373.

Ji, Y. et al. (Nov. 2002) "Processing and Mechanical Properties of $Al_2O_3$-5 vol.% Cr Nanocomposites," *Journal of the European Ceramic Society* 22(12):1927-1936.

Jouet, R. J. et al. (Jan. 25, 2005). "Surface Passivation of Bare Aluminum Nanoparticles Using Perfluoroalkyl Carboxylic Acids," *Chem. Mater.*17(11):2987-2996.

Kenvin, J. C. et al. (1992). "Supported Catalysts Prepared from Mononuclear Copper Complexes: Catalytic Properties", *J. Catalysis* 135:81-91.

Konrad, H. et al. (1996). "Nanostructured Cu—Bi Alloys Prepared by Co-Evaporation in a Continuous Gas Flow," *NanoStructured Materials* 7(6):605-610.

Kim, N. Y. et al. (Mar. 5, 1997). "Thermal Derivatization of Porous Silicon with Alcohols," *J. Am. Chem. Soc.* 119(9):2297-2298.

Kwon, Y.-S. et al. (Apr. 30, 2003). "Passivation Process for Superfine Aluminum Powders Obtained by Electrical Explosion of Wires," *Applied Surface Science* 211:57-67.

Lakis, R. E. et al. (1995). "Alumina-Supported Pt—Rh Catalysts: I. Microstructural Characterization," *Journal of Catalysis* 154: 261-275.

Lamouroux, E. et al. (2007). "Identification of Key Parameters for the Selective Growth of Single or Double Wall Carbon Nanotubes on FeMo/$Al_2O_3$ CVD Catalysts," *Applied Catalysts A: General* 323: 162-173.

Langner, A. et al. (Aug. 25, 2005). "Controlled Silicon Surface Functionalization by Alkene Hydrosilylation," *J. Am. Chem. Soc.* 127(37):12798-12799.

Li, D. et al. (Apr. 9, 2005). "Environmentally Responsive "Hairy" Nanoparticles: Mixed Homopolymer Brushes on Silica Nanoparticles Synthesized by Living Radical Polymerization Techniques," *J. Am. Chem. Soc.* 127(7):6248-6256.

Li, J-G. et al. (2009). "Cobalt-Doped $TiO_2$ Nanocrystallites: Radio-Frequency Thermal Plasma Processing, Phase Structure, and Magnetic Properties," *J. Phys. Chem.* 113 (19): 8009-8015.

Li, X. et al. (May 25, 2004). "Surface Functionalization of Silicon Nanoparticles Produced by Laser-Driven Pyrolysis of Silane Followed by HF—$HNO_3$ Etching," *Langmuir* 20(11):4720-4727.

Liao, Y.-C. et al. (Jun. 27, 2006). "Self-Assembly of Organic Monolayers on Aerosolized Silicon Nanoparticles," *J.Am. Chem. Soc.* 128(28):9061-9065.

Liu, S.-M. et al. (Jan. 13, 2006). "Enhanced Photoluminescence from Si Nano-Organosols by Functionalization With Alkenes and Their Size Evolution," *Chem. Mater.* 18(3):637-642.

Luo, J. et al. (2008). "Core/Shell Nanoparticles as Electrocatalysts for Fuel Cell Reactions," *Advanced Materials* 20: 4342-4347.

Magdassi, S. et al. (Apr. 2010). "Triggering the Sintering of Silver Nanoparticles at Room Temperature," *ACS Nano* 4(4): 1943-1948.

Martinez-Hansen, V. et al. (2009). "Development of Aligned Carbon Nanotubes Layers Over Stainless Steel Mesh Monoliths," *Catalysis Today* 147S: S71-S75.

Mignard, D. et al. (2003). "Methanol Synthesis from Flue-Gas $CO_2$ and Renewable Electricity: A Feasibility Study," *International Journal of Hydrogen Energy* 28: 455-464.

Mühlenweg, H. et al. (2004). "Gas-Phase Reactions—Open Up New Roads to Nanoproducts," *Degussa ScienceNewsletter* No. 8, pp. 12-16.

Nagai, Y. et al. (Jul. 3, 2006). "Sintering Inhibition Mechanism of Platinum Supported on Ceria-Based Oxide and Pt-Oxide-Support Interaction," *J. Catalysis* 242:103-109.

NASA (2009). "Enthalpy," Article located at http://www.grc.nasa.gov/WWW/K-12/airplane/enthalpy.htrnl, published by National Aeronautics and Space Administration on Nov. 23, 2009, 1 page.

Neiner, D. (Aug. 5, 2006). "Low-Temperature Solution Route to Macroscopic Amounts of Hydrogen Terminated Silicon Nanoparticles," *J. Am. Chem. Soc.* 128:11016-11017.

Netzer, L. et al. (1983). "A New Approach to Construction of Artificial Monolayer Assemblies," *J. Am. Chem. Soc.* 105(3):674-676.

Panchula, M. L. et al. (2003). "Nanocrystalline Aluminum Nitride: I, Vapor-Phase Synthesis in a Forced-Flow Reactor," *Journal of the American Ceramic Society* 86(7): 1114-1120.

Park, H.-Y. et al. (May 30, 2007). "Fabrication of Magnetic Core@Shell Fe Oxide@Au Nanoparticles for Interfacial Bioactivity and Bio-Separation," *Langmuir* 23: 9050-9056.

Park, N.-G. et al. (Feb. 17, 2004). "Morphological and Photoelectrochemical Characterization of Core-Shell Nanoparticle Films for Dye-Sensitized Solar Cells: Zn—O Type Shell on $SnO_2$ and $TiO_2$ Cores," *Langmuir* 20: 4246-4253.

"Plasma Spray and Wire Flame Spray Product Group," located at http://www.processmaterials.com/spray.html, published by Process Materials, Inc., last accessed Aug. 5, 2013, 2 pages.

"Platinum Group Metals: Annual Review 1996" (Oct. 1997). Engineering and Mining Journal, p. 63.

Rahaman, R. A. et al. (1995). "Synthesis of Powders," in *Ceramic Processing and Sintering*. Marcel Decker, Inc., New York, pp. 71-77.

Sailor, M. J. (1997). "Surface Chemistry of Luminescent Silicon Nanocrystallites," *Adv. Mater.* 9(10):783-793.

Schimpf, S. et al. (2002). "Supported Gold Nanoparticles: In-Depth Catalyst Characterization and Application in Hydrogenation and Oxidation Reactions," *Catalysis Today* 2592: 1-16.

Stiles, A. B. (Jan. 1, 1987). "Manufacture of Carbon-Supported Metal Catalysts," in *Catalyst Supports and Suppoorted Catalysts*, Butterworth Publishers, MA, pp. 125-132.

Strobel, R. et al. (2003). "Flame-made Platinum/Alumina: Structural Properties and Catalytic Behaviour in Enantioselective Hydrogenation," *Journal of Catalysis* 213: 296-304.

Subramanian, S. et al. (1991). "Structure and Activity of Composite Oxide Supported Platinum-Iridium Catalysts," *Applied Catalysts* 74: 65-81.

Tao, Y.-T. (May 1993). "Structural Comparison of Self-Assembled Monolayers of n-Alkanoic Acids on the surfaces of Silver, Copper, and Aluminum," *J. Am. Chem. Soc.* 115(10):4350-4358.

Ünal, N. et al. (Nov. 2011). "Influence of WC Particles on the Microstructural and Mechanical Properties of 3 mol% $Y_2O_3$ Stabilized $ZrO_2$ Matrix Composites Produced by Hot Pressing," *Journal of the European Ceramic Society* (31)13: 2267-2275.

Vardelle, A. et al. (1996). "Coating Generation: Vaporization of Particles in Plasma Spraying and Splat Formation," Universite de Limoges, 123 Avenue A. Thomas 87000, Limoges, France, *Pure & Appl. Chem.* 68(5):1093-1099.

Vardelle, M. et al. (Jun. 1991). "Experimental Investigation of Powder Vaporization in Thermal Plasma Jets," *Plasma Chemistry and Plasma Processing* 11(2):185-201.

Viswanathan, V. et al. (2006). "Challenges and Advances in Nanocomposite Processing Techniques," *Materials Science and Engineering R* 54: 121-285.

Wan, J. et al. (2005). "Spark Plasma Sintering of Silicon Nitride/Silicon Carbide Nanocomposites with Reduced Additive Amounts," *Scripta Materialia* 53: 663-667.

Yoshida, T. (1994). "The Future of Thermal Plasma Processing for Coating", *Pure & Appl. Chem.* 66(6):1223-1230.

Zou, J. et al. (Jun. 4, 2004). "Solution Synthesis of Ultrastable Luminescent Siloxane-Coated Silicon Nanoparticles," *Nano Letters* 4(7):1181-1186.

Non Final Office Action mailed on Feb. 19, 2010, for U.S. Appl. No. 12/152,109, filed May 9, 2008, Biberger et al., 17 pages.

Final Office Action mailed on Jan. 7, 2010, for U.S. Appl. No. 12/001,643, filed Dec. 11, 2007, for Biberger et al., 9 pages.

Advisory Action mailed on Mar. 4, 2010, for U.S. Appl. No. 12/001,643, filed Dec. 11, 2007, for Biberger et al., 9 pages.

Final Office Action mailed on Feb. 26, 2010, for U.S. Appl. No. 12/474,081, filed May 28, 2009, for Biberger et al., 7 pages.

Advisory Action mailed on May 4, 2010, for U.S. Appl. No. 12/474,081, filed May 28, 2009, for Biberger et al., 7 pages.

(56) References Cited

OTHER PUBLICATIONS

Non Final Office Action mailed on Jun. 23, 2010, for U.S. Appl. No. 12/474,081, filed May 28, 2009, for Biberger et al., 12 pages.
Non Final Office Action mailed on Dec. 8, 2010, for U.S. Appl. No. 12/474,081, filed on May 28, 2009, for Biberger et al., 14 pages.
Final Office Action mailed on Oct. 14, 2010, for U.S. Appl. No. 12/001,602, filed Dec. 11, 2007, for Biberger et al., 13 pages.
Final Office Action mailed on Jun. 22, 2011, for U.S. Appl. No. 12/001,602, filed Dec. 11, 2007, for Biberger et al., 16 pages.
U.S. Appl. No. 12/152,084, filed May 9, 2008, for Biberger.
U.S. Appl. No. 13/028,693, filed Feb. 16, 2011, for Biberger.
U.S. Appl. No. 12/152,111, filed May 9, 2008, for Biberger et al.
U.S. Appl. No. 12/968,239, filed Dec. 14, 2010, for Biberger.
U.S. Appl. No. 12/969,128, filed Dec. 15, 2010, for Biberger.
U.S. Appl. No. 12/969,306, filed Dec. 15, 2010, for Lehman et al.
U.S. Appl. No. 12/969,447, filed Dec. 15, 2010, for Biberger et al.
U.S. Appl. No. 12/001,644, filed Dec. 11, 2007, for Biberger et al.
U.S. Appl. No. 12/969,457, filed Nov. 15, 2010, for Leamon et al.
U.S. Appl. No. 12/954,813, filed Nov. 26, 2010, for Biberger.
U.S. Appl. No. 12/954,822, filed Nov. 26, 2010, for Biberger.

\* cited by examiner

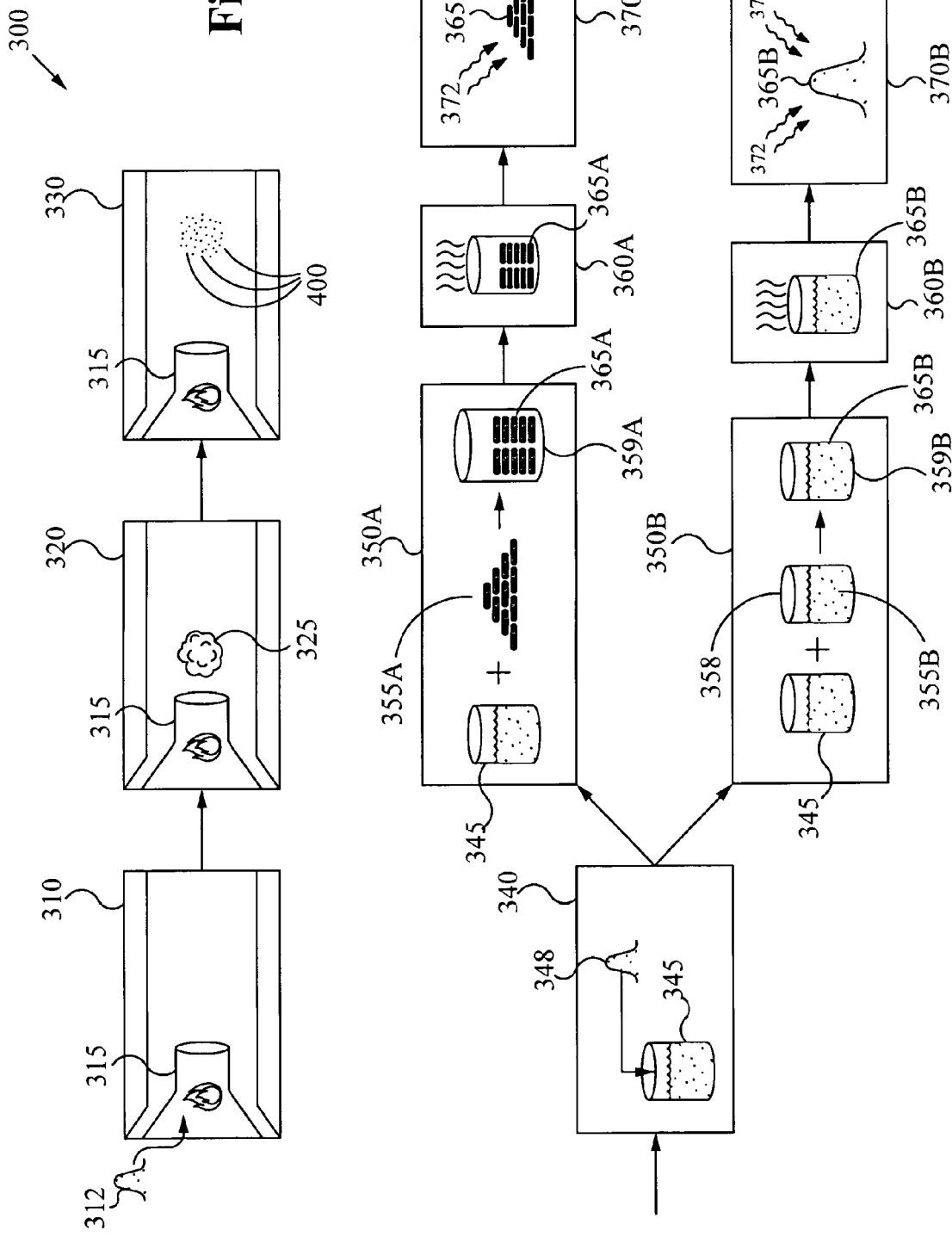

METHOD AND SYSTEM FOR FORMING PLUG AND PLAY OXIDE CATALYSTS

CROSS-REFERENCE TO RELATED APPLICATIONS

This patent application is a continuation application of U.S. patent application Ser. No. 13/921,066, filed Jun. 18, 2013, which is a continuation application of U.S. patent application Ser. No. 12/001,644, filed Dec. 11, 2007, now U.S. Pat. No. 8,481,449, which claims priority benefit of U.S. Provisional Patent Application No. 60/999,057, filed Oct. 15, 2007. The entire contents of those applications are hereby incorporated by reference herein.

BACKGROUND OF THE INVENTION

In the oil refining and fine chemical industries, catalysts are required to transform one chemical or one material into another. For example, to make cyclohexane from benzene, benzene is passed through porous ceramic supports that have been impregnated with catalysts designed and configured to hydrogenate it into cyclohexane. In one particular process, platinum is nitrated and impregnated onto supports in the wet chemical process 100 shown in FIG. 1. A platinum group metal, such as platinum, osmium, ruthenium, rhodium, palladium or iridium, is collected in step 101. For the sake of brevity, platinum will be discussed herein but it will be apparent to those of ordinary skill in the art that different platinum group metals can be used to take advantage of their different properties. Since blocks of elemental platinum are not useable as a catalyst, the platinum is nitrated in the step 102, forming a salt, specifically $PtNO_3$. The nitration is typically performed using well known methods of wet chemistry. The $PtNO_3$ is dissolved into a solvent such as water in a step 103, causing the $PtNO_3$ to dissociate into $Pt+$ and $NO_3-$ ions. In the step 104, the salt is adsorbed onto the surfaces of supports 104B through transfer devices 104A, such as pipettes. An example of a support 104B is shown in FIG. 2. Generally, a support 104B is a highly porous ceramic material that is commercially available in a vast array of shapes, dimensions and pore sizes to accommodate particular requirements of a given application. The supports 104B are dried to remove water then transferred to an oven for an air calcining step 105. In the oven, the supports 104B are exposed to heat and optionally pressure that causes the $Pt+$ to coalesce into elemental Pt particles on the surfaces of the supports 104B. In the step 106, end product catalysts are formed. The end product is a support 104B that is impregnated with elemental platinum. These supports are generally used in catalytic conversion by placing them in reactors of various configurations. For example, benzene is passed through the supports 104B which convert the benzene into cyclohexane in the fine chemical industry. In the oil refining industry, the supports are used in a similar fashion. The process steps are used to convert crude oil into a useable fuel or other desirable end product. The process described in FIG. 1 has opportunities for improvement. Although the platinum sticks sufficiently well to the surface of the support 104b, platinum atoms begin to move and coalesce into larger particles at the temperatures that catalysis generally occurs. It is understood that the effectiveness and activity of a catalyst are directly proportional to the size of the catalyst particles on the surface of the support. As the particles coalesce into larger clumps, the particle sizes increase, the surface area of the catalyst decreases and the effectiveness of the catalyst is detrimentally affected. As the effectiveness of the catalyst decreases, the supports 104B must be removed from the reactors and new supports added. During the transition period, output is stopped and overall throughput is adversely affected. Also, platinum group metal catalysts are very expensive, and every addition of new supports comes at great cost. What is needed is a plug and play catalyst that is usable in current oil refineries and fine chemical processing plants, allowing an increase in throughput and decrease in costs.

SUMMARY OF THE INVENTION

A method of making an oxide catalyst comprises providing a quantity of oxygen containing nanoparticles, providing a quantity of supports, and combining the supports with the nanoparticles. In some embodiments, the supports comprise voids and pores. Preferably, providing a quantity of nanoparticles comprises loading a quantity of at least one precursor material into a plasma gun, vaporizing the at least one precursor material and quenching the at least one precursor material. The precursor material comprises any among a list of a metal, an oxide, a salt, a carbon compound and any combination thereof. Alternatively, providing a quantity of nanoparticles comprises loading a quantity of at least one catalyst material into a plasma gun, vaporizing the at least one catalyst material and quenching the at least one catalyst material. Preferably, combining the supports and nanoparticles comprises suspending the nanoparticles in a solution, thereby forming a suspension and mixing the suspension with a quantity of the supports. Alternatively, combining the supports and nanoparticles comprises suspending the nanoparticles in a solution, thereby forming a suspension and mixing the suspension with a slurry having porous supports suspended therein. The solution further comprises a dispersant. The slurry comprises any among an organic solvent, an aqueous solvent, or a combination thereof. Preferably, the method further includes drying the supports. Also, the method further comprises exposing the supports to any one of heat, pressure or a combination thereof, thereby calcining the nanoparticles onto the supports.

A system for forming an oxide catalyst comprises means for providing a quantity of oxygen containing nanoparticles, means for collecting the nanoparticles, means for forming a suspension by mixing the nanoparticles into a liquid and means for combining the suspension with a quantity of supports. Preferably, the means for providing a quantity of nanoparticles comprises means for loading a quantity of at least one precursor material into a plasma gun, means for vaporizing the precursor material thereby forming a vapor cloud and means for quenching the vapor cloud thereby forming solid nanoparticles. Alternatively, the means for providing a quantity of nanoparticles comprises means for loading a quantity of at least one catalyst material into a plasma gun, means for vaporizing the catalyst material thereby forming a vapor cloud and means for quenching the vapor cloud thereby forming solid nanoparticles. The system further comprises means for drying the supports. The system also comprises means for exposing the supports to heat, thereby calcining the nanoparticles onto the supports. Preferably, the means for combining the suspension with supports comprises means for impregnating supports with the suspension. Alternatively, the means for combining the suspension with the supports comprises means for mixing the suspension with a slurry having supports. The slurry comprises any among an organic solvent, and aqueous solvent, and a combination thereof. Preferably, the suspension comprises an adjunct configured to cause the nanoparticles to repel each other in the solvent thereby suspending in the solvent.

BRIEF DESCRIPTION OF THE DRAWINGS

The invention is better understood by reading the following detailed description of an exemplary embodiment in conjunction with the accompanying drawings.

FIG. 3 shows the preferred embodiment of a novel process for forming a support for use in heterogeneous catalysis.

DETAILED DESCRIPTION OF THE INVENTION

Figure 1:
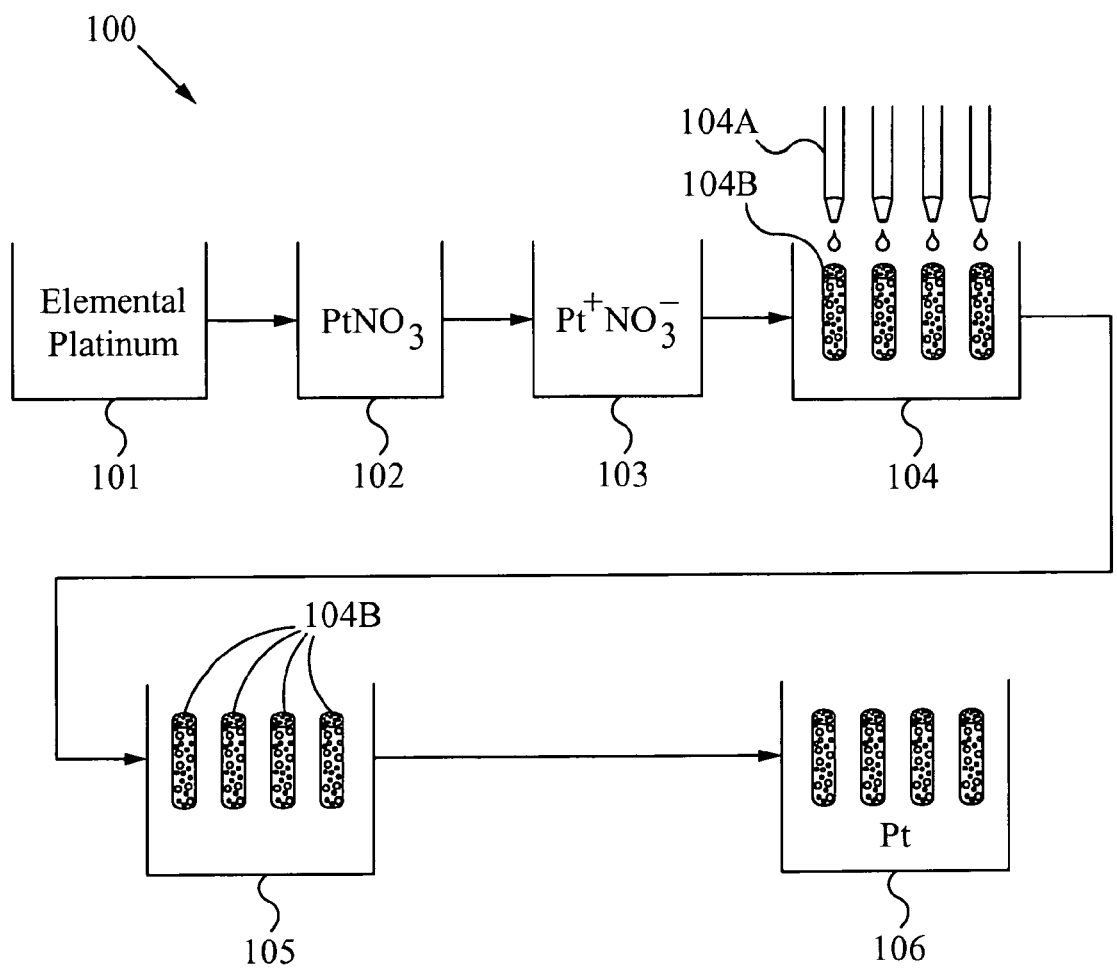
FIG. 1 prior art illustrates an existing process for forming a useful support for use in heterogenous catalysis.

Reference will now be made in detail to implementations of the present invention as illustrated in the accompanying drawings. The drawings may not be to scale. The same reference indicators will be used throughout the drawings and the following detailed description to refer to identical or like elements. In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application, safety regulations and business related constraints, and that these specific goals will vary from one implementation to another and from one developer to another. Moreover, it will be appreciated that such a development effort will be a routine undertaking of engineering for those of ordinary skill in the art having the benefit of this disclosure.

The following description of the invention is provided as an enabling teaching which includes the best, currently known embodiment. One skilled in the relevant arts, including but not limited to chemistry and physics, will recognize that many changes can be made to the embodiment described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and may even be desirable in certain circumstances, and are a part of the present invention. Thus, the following description is provided as illustrative of the principles of the present invention and not in limitation thereof, since the scope of the present invention is defined by the claims. The terms "nanoparticle," "nanoparticle powder," and "nano powder" are generally understood by those of ordinary skill to encompass a quantity of material comprising particles on the order of nanometers in diameter, as described herein.

FIG. 3 illustrates the inventive steps for a process 300 of forming a "plug and play" catalyst for use in such industries as chemical manufacturing. The method begins at the step 310. A quantity of at least one precursor material 312 is loaded into a plasma gun 315. Preferably, the precursor 312 comprises any among an oxide, a metal, a metal oxide, a metal salt, a chlorine compound, phosphorous compound, or any combination thereof. Alternatively, an oxide catalyst is loaded into the plasma gun 315. Oxides are well known and studied in the field of chemistry. Many oxide combinations exist, each having applications in industry. This disclosure focuses on oxides having catalytic properties. Oxides having catalytic properties include metal oxides, nonmetal oxides, and oxide-oxide bonded particles. Particularly, some oxides are used in heterogeneous catalysis, wherein the catalyst is in a different phase than the reactants. Heterogeneous catalysts provide a surface for the chemical reaction to take place on or otherwise activate the reaction. Next, in the step 320, the plasma gun 315 vaporizes the precursor 312 to form a vapor cloud 325. By way of example, if the desired oxide catalyst is lanthanum iron oxide, multiple permutations of precursor 312 are amenable to that end. One permutation includes loading a quantity of pre-formed lanthanum iron oxide, a commercially available material, into the plasma gun 315. Another permutation includes loading a quantity of lanthanum oxide and iron into the gun 315. In still another permutation, lanthanum and iron are loaded into the plasma gun 315 and the resulting vapor cloud 325 is combined with ambient oxygen. Alternatively, oxygen or an oxygen containing compound is injected into the reaction chamber. Also, more complex oxides having multiple components are contemplated. It will be apparent to those of ordinary skill that many different permutations are amenable to the process described herein with a vast array of starting compounds.

Figure 4A:
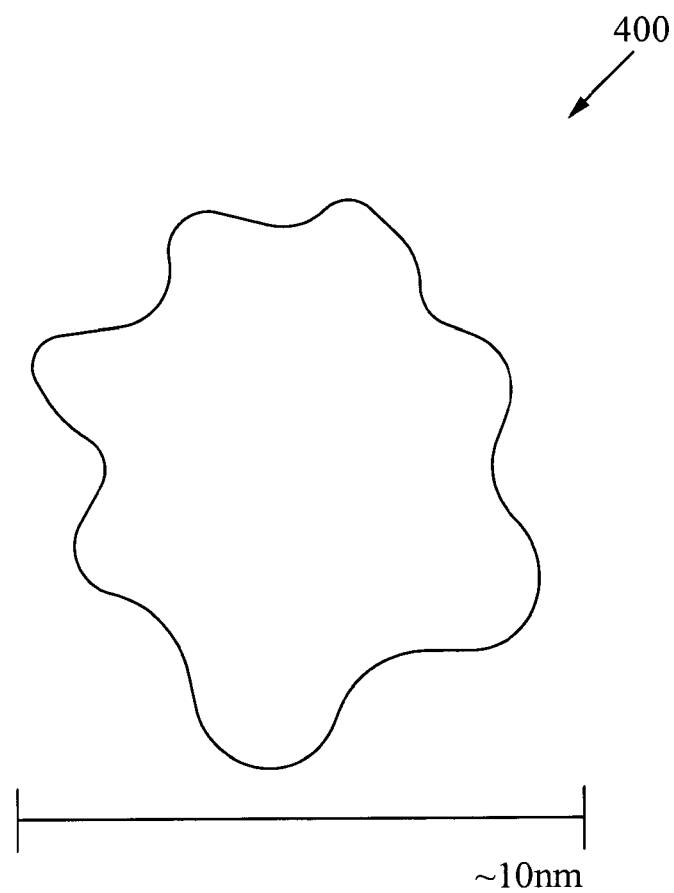
FIG. 4A shows an example of a nanoparticle formed as part of the process of FIG. 3.

Still referring to FIG. 3, the resulting vapor cloud 325 is then put through a quenching step 330. Preferably, the quenching step occurs in a highly turbulent quench chamber to facilitate rapid, even, consistent quenching of the vapor 325 into precipitate nanoparticles 400. Such a rapid quench chamber is described in detail in U.S. patent application Ser. No. 12/151,935, filed on May 8, 2008, which published as U.S. Patent Publication No. 2008-0277267 and is hereby incorporated by reference. As the gaseous oxide particles cool, they solidify into nanoparticles 400. An example of a resulting nanoparticle 400 is shown in FIG. 4A. The particles 400 will generally be in the range of 0.5 to 200 nm in size, and can be as small as a molecular length of the catalyst material and as large as would be achievable by ball milling. The particle size is able to be varied with varying starting materials, vaporization speeds, quench speeds and plasma temperatures.

In some embodiments, the process 300 continues with step 340, where the nanoparticles 400 are combined with a liquid to form a dispersion 345. Preferably, a liquid that will not react with the catalyst or precursor materials is used. Some appropriate liquids are aqueous solutions or organic solutions employing solvents such as alcohols, ethers, hydrocarbons, esters, amines, or the like. Since the nanoparticles 400 are small, other precautions are generally taken to ensure that they suspend evenly within the dispersion. To that end, an adjunct 348 is able to be added to the dispersion. The adjunct 348, also referred to commonly in the art as a surfactant or dispersant, adheres to the nanoparticles 400 and causes them to repel each other, thereby causing the nanoparticles 400 to suspend evenly in the dispersion 345. The dispersion 345 is also referred to as a suspension.

Figure 2:
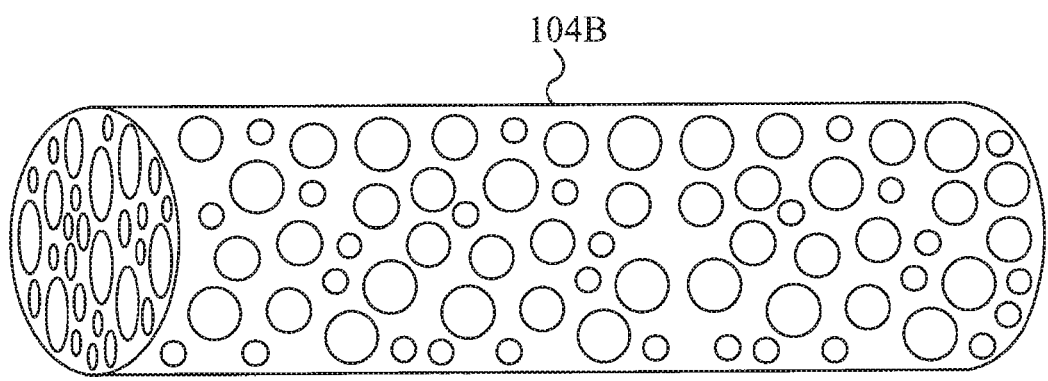
FIG. 2 prior art shows a porous support generally used as a support in heterogeneous catalysis.

Referring back to FIG. 3, it is important to note that nanoparticles 400 such as the one shown in FIG. 4 are not generally compatible with existing processes for chemical conversion. For compatibility with existing processes, the nanoparticles 400 are bonded to a support. When the nanoparticles 400 are bonded to a support, nanoparticle 400 provides a surface where reactions are able to take place or where reactions are activated. To that end, more steps are taken to bring the nanoparticles 400 to a useable form. To bring the nanoparticles 400 closer to a usable catalyst, the nanoparticles 400 are impregnated onto supports 355. The supports 355 are also known to those skilled in the relevant art as porous oxides. Alternatively, the supports 355 are also referred to as extrudates because they are generally made using an extrusion process. The supports 355 are similar to the supports 104b in FIGS. 1 and 2. Such supports have found utility due to their highly accessible and large surface area, as high as 250 $m^2/g$. In alternative embodiments, a macroscopic support particle is able to be used. In such an embodiment, the size of the macroscopic support particle is selected to provide maximum surface area to which nanoparticles 400 are bonded or fixed. The step 350A shows the preferred embodiment of achieving the impregnation. The dispersion 345 is combined with a quantity of substantially dry porous supports 355A to form a mixture 359A. Alternatively, as shown in the step 350B, the dispersion 345 is combined with a slurry 358 having macroscopic support particles 355B suspended therein, thereby forming the mixture 359B. The slurry 358 is able to be a suspension of water, alcohol, or any suitable organic or inorganic liquid which will not react with the macroscopic supports 355B or nanoparticles 400. In the step 350A, capillary forces will draw in the dispersion 345, and in turn the nanoparticles 400, into the various voids and pores within the structure of the porous supports 355A, thereby forming impregnated porous supports 365A. To aid in the impregnation, the mixture can be agitated or subjected to heat or pressure. In the step 350B, nanoparticles 400 come to rest on the surfaces of macroscopic supports thereby forming impregnated macro supports 365B. In some embodiments, the steps 350A or 350B are repeated at least once for enhanced impregnation.

Figure 4B:
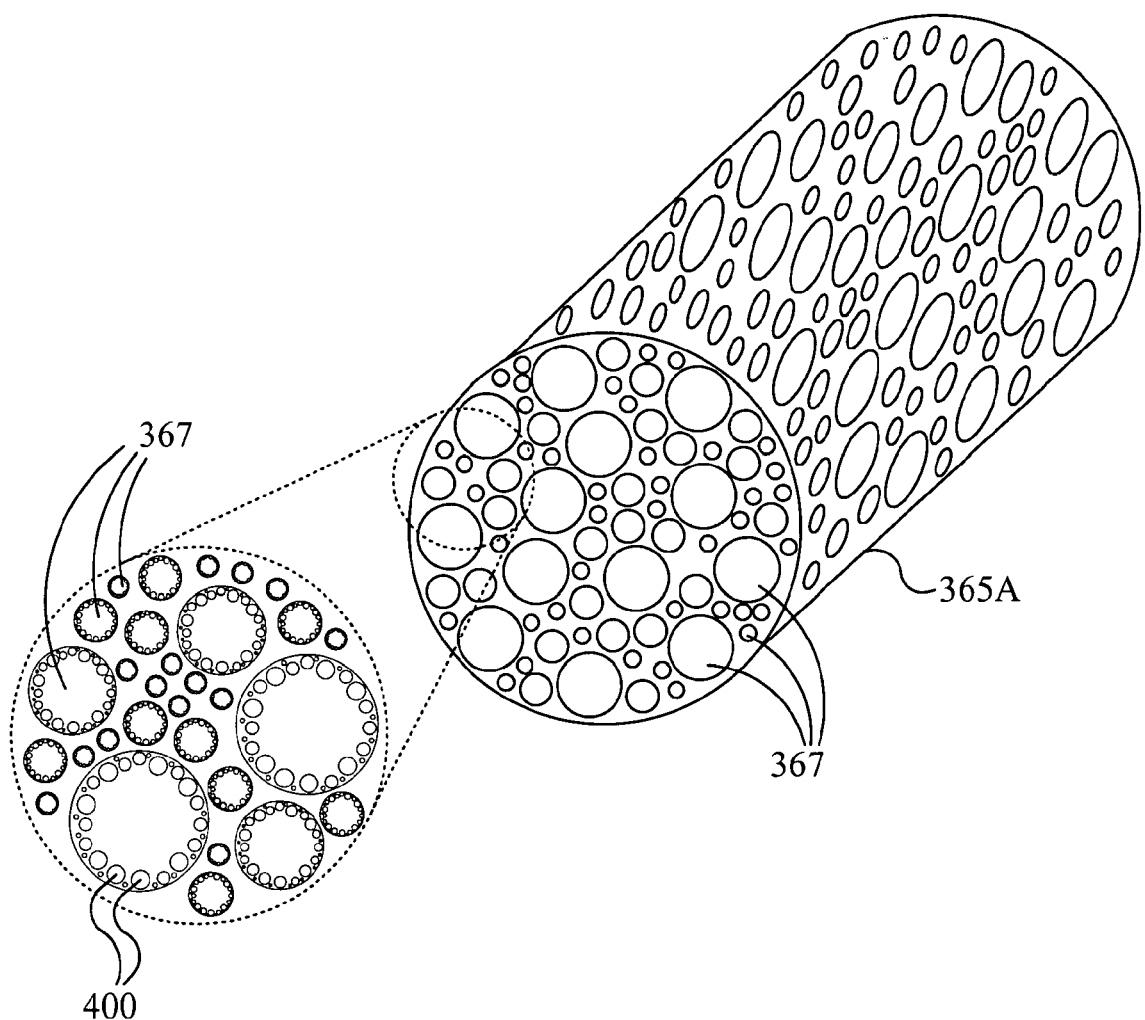
FIG. 4B shows a close up of an impregnated porous support.
Figure 4C:
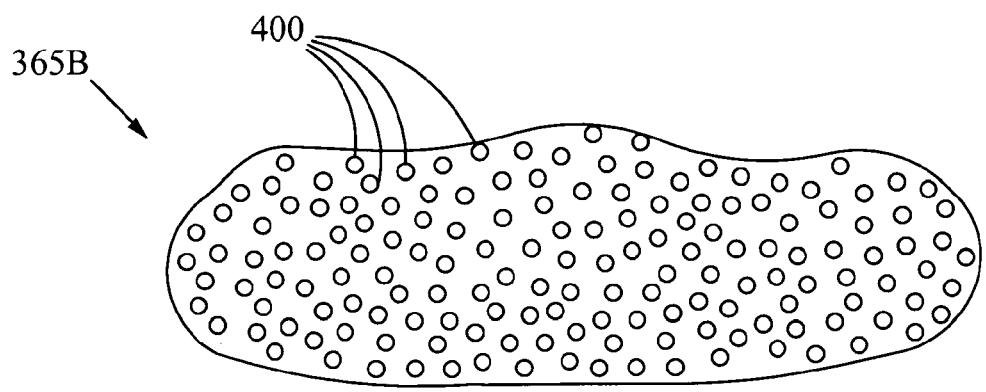
FIG. 4C shows a close up of an impregnated macro support.

Next, in the steps 360A and 360B, the impregnated porous supports 365A or macro supports 365B are allowed to dry. A close up view the impregnated porous support 365A is shown in FIG. 4B. As the liquid in the dispersion 345 evaporates, the nanoparticles 400 settle onto the surface of the support 365A and into the pores 367 within the support 365A. FIG. 4C shows an example of an impregnated macro support 365B. As the liquids in the dispersion 345 and slurry 358 dry, nanoparticles 400 settle onto the surface of the macro support 365B. When the impregnated porous supports 365A or macro supports 365B dry, electrostatic interactions and other non covalent forces between the nanoparticles 400 and the porous supports 365A or macro supports 365B effectuate some adhesion. Advantageously, such forces cause the nanoparticles 400 to stick onto the surfaces and pores 367 of the supports 365A or 365B, and effectuate transfer of the supports 365 through the remainder of the process 300. Referring back to FIG. 3, a calcining step 370A or 370B is performed to form oxide-oxide bonds between the nanoparticles 400 and the impregnated supports 365A or 365B by exposing them to heat 372, pressure 375, or a combination thereof. The calcining temperature is generally from 350 to 1000 degrees centigrade, and the pressure is on the order of ambient atmosphere to several atmospheres.

Due to the physical and chemical bond between the supports 365A and 365B and the nanoparticles 400, islands of nanoparticles 400 that are bonded, fixed or otherwise pinned to the surfaces of the supports 365A or 365B will not migrate and coalesce during catalytic conversion. The surface area for catalysis remains high, and therefore the catalytic activity remains high. In effect, operations such as fine chemical plants and oil refineries will not be required to stop operations and swap out ineffective catalyst supports with fresh catalyst supports with the same frequency as existing processes, thereby increasing throughput at the plants and refineries and reducing their overall cost of operation.

Figure 5:
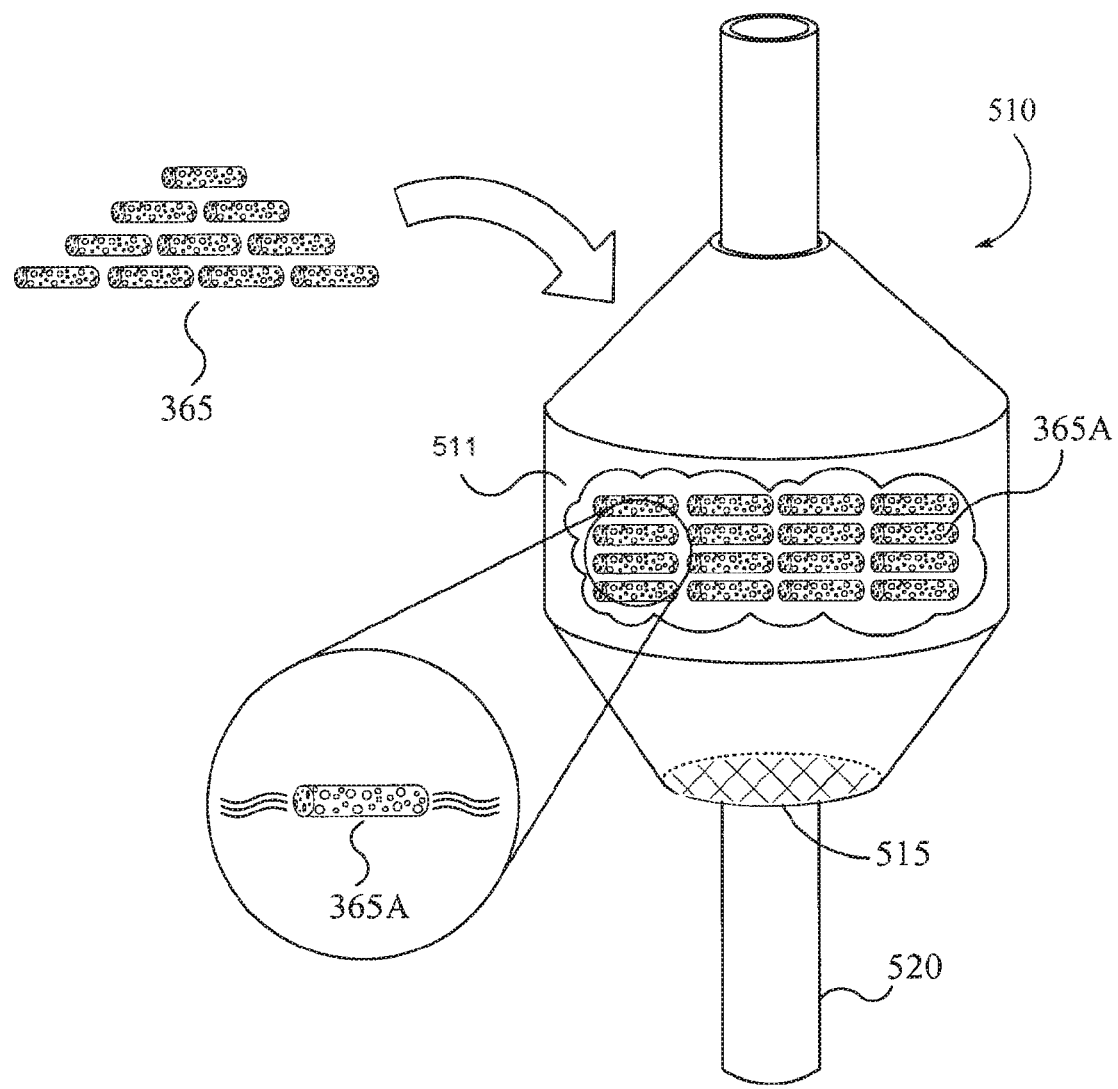
FIG. 5 shows an example of the supports being used as heterogeneous catalysts.

FIG. 5 shows an example of the impregnated porous supports 365A being used in the fine chemical industry to hydrogenate benzene into cyclohexane. Macro supports 365B are able to be used as well. Although this example details use in the fine chemical industry, it will be apparent to those of ordinary skill in the arts of chemistry, chemical engineering, or the like that any process using heterogeneous catalysis is able to benefit from this disclosure. An amount of impregnated porous supports 365A is loaded into a reactor 510. Preferably, the reactor 510 has a mesh opening 515 on one end wherein the meshing has a smaller opening pitch than the size of the supports 365 such that the supports 365 do not fall through the opening 515. Benzene is passed into the vat 511 via the conduit 520. As the benzene passes through the vat 511, the benzene fills into the voids and pores of the support 365A.

Figure 5A:
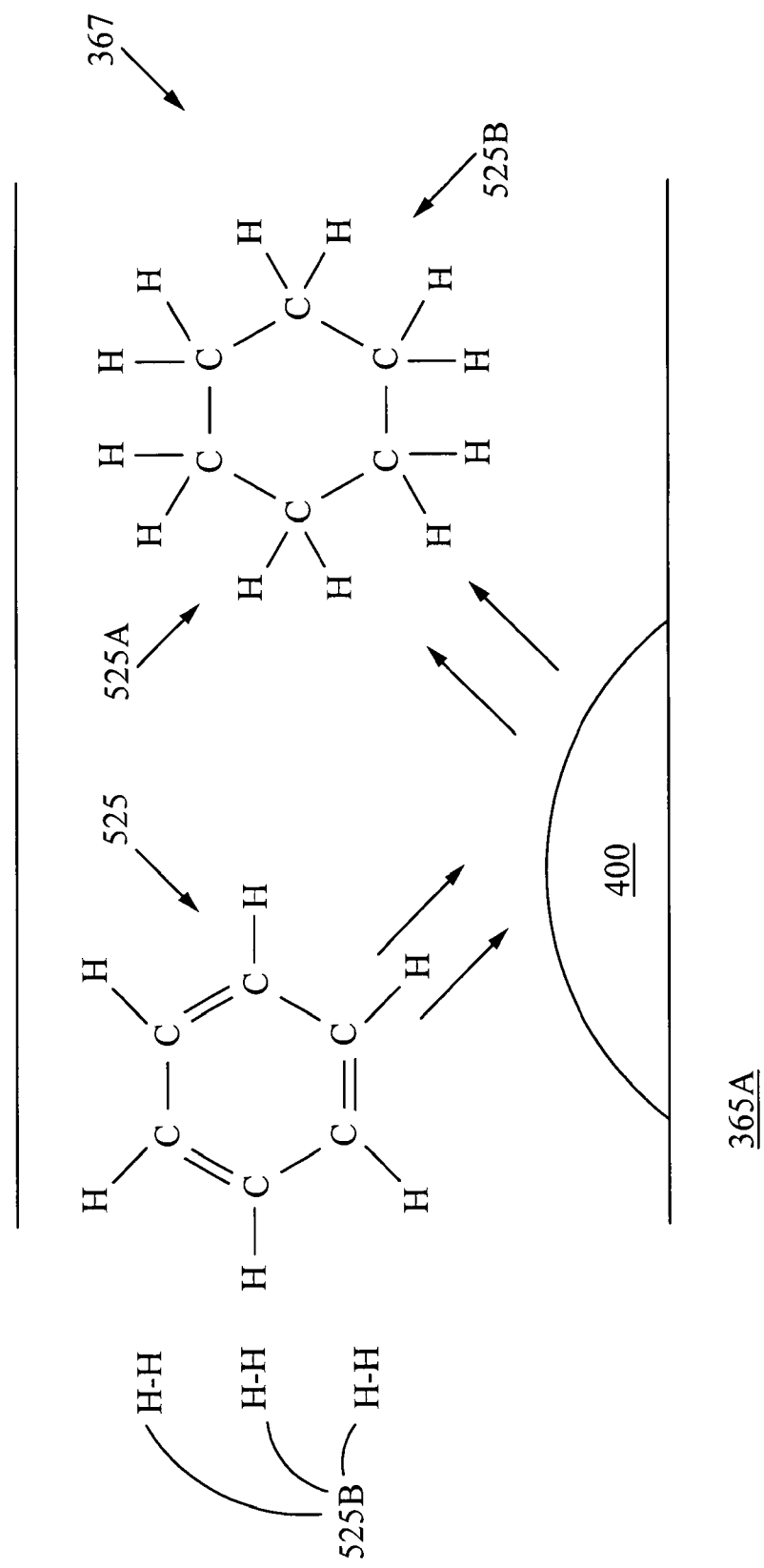
FIG. 5A shows the hydrogenation of benzene into cyclohexane.

FIG. 5A shows an example of a benzene molecule 525 being hydrogenated into cyclohexane 525A in a cross section of a pore 367. When the benzene molecule 525 comes into contact with the nanoparticle 400 that is bonded to the surface of the support 365A, nanoparticle 400 will effectuate hydrogenation of the benzene molecule 525 and hydrogen molecules 525B into cyclohexane 525A without losing any energy to heat or risking uncontrolled burning or combustion.

We claim:
1. A supported catalyst, comprising:
   a. support structures, wherein the support structure comprises a porous oxide; and
   b. nanoparticles bonded to the support structures, wherein the nanoparticles comprise an oxide catalyst;
   wherein the nanoparticles are attached to the support structures by an oxide-oxide bond.
2. The supported catalyst of claim 1, wherein the oxide catalyst comprises a metal oxide.
3. The supported catalyst of claim 2, wherein the oxide catalyst comprises lanthanum iron oxide.
4. The supported catalyst of claim 1, wherein the nanoparticles are prepared using plasma.
5. The supported catalyst of claim 1, wherein the support structures are macroscopic particles.
6. The supported catalyst of claim 1, wherein the nanoparticles are about 0.5 nanometers to about 200 nanometers in diameter.
7. The supported catalyst of claim 1, wherein the nanoparticles are on the surface and in the pores of the support structures.
8. The supported catalyst of claim 7, wherein the nanoparticles are deposited on the surface and in the pores of the support structures by suspending the nanoparticles in a solution to form a suspension, and mixing the suspension with the support structures.
9. The supported catalyst of claim 8, wherein the solution further comprises a dispersant.

10. The supported catalyst of claim 8, wherein the suspension of nanoparticles mixed with the support structures is dried, then exposed to heat, pressure, or a combination of heat and pressure to calcine the nanoparticles onto the support structures.

11. The supported catalyst of claim 7, wherein the nanoparticles are deposited on the surface and in the pores of the support structures by suspending the nanoparticles in a solution to form a suspension, and mixing the suspension with a slurry having the support structures suspended therein.

12. The supported catalyst of claim 11, wherein the solution further comprises a dispersant.

13. The supported catalyst of claim 1, wherein the nanoparticles comprise a metal oxide formed from a precursor material, wherein the precursor material is selected from the group consisting of a metal, a metal oxide, a metal salt, a carbon compound, a chlorine compound, a phosphorous compound, and any combination thereof.

14. The supported catalyst of claim 1, wherein the oxide-oxide bond is formed by calcination.

\* \* \* \* \*